United States Patent
Decout et al.

(10) Patent No.: US 7,514,404 B2
(45) Date of Patent: Apr. 7, 2009

(54) PNA-NEAMINE CONJUGATES AND METHODS FOR PRODUCING AND USING THE SAME

(75) Inventors: Jean-Luc Decout, Vaulnaveys le Haut (FR); Virendra N. Pandey, Parsippany, NJ (US); Emmanuel Riguet, Saint Thomas en Royans (FR)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 123 days.

(21) Appl. No.: 10/581,949

(22) PCT Filed: Dec. 6, 2004

(86) PCT No.: PCT/US2004/040714

§ 371 (c)(1),
(2), (4) Date: Dec. 28, 2006

(87) PCT Pub. No.: WO2005/060573

PCT Pub. Date: Jul. 7, 2005

(65) Prior Publication Data

US 2007/0225239 A1 Sep. 27, 2007

(51) Int. Cl.
*A61K 38/02* (2006.01)
*C07H 15/224* (2006.01)
*C07K 2/00* (2006.01)

(52) U.S. Cl. .............................. 514/8; 514/36; 530/322; 536/16.6

(58) Field of Classification Search .................. None
See application file for complete search history.

(56) References Cited

U.S. PATENT DOCUMENTS

| | | | | |
|---|---|---|---|---|
| 4,008,362 | A | 2/1977 | Akita et al. | 536/17 |
| 5,712,096 | A * | 1/1998 | Stern et al. | 435/6 |
| 2004/0063618 | A1* | 4/2004 | Manoharan | 514/8 |
| 2005/0019926 | A1* | 1/2005 | Gonda et al. | 435/455 |

FOREIGN PATENT DOCUMENTS

WO WO 00/39139 7/2000

OTHER PUBLICATIONS

Pirollo et al. Antisense therapeutics: from theory to clinical practice. Pharmacology & Therapeutics. 2003. vol. 99, pp. 55-77.*
Riguet et al. A Peptide Nucleic Acid-Neamine Conjugate ... Journal of Medicinal Chemistry. 2004. vol. 47, No. 20, pp. 4806-4809.*
Arya et al., "Neomycin Binding to Watson-Hoogsteen (W-H) DNA Triplex Groove: A Model", J. Am. Chem. Soc. 2003 125:3733-3744.
Carriere et al., "Inhibition of protein synthesis by aminoglycoside-arginine conjugates", RNA 2002 8:1267-1279.
Charles et al., Corrigendum to 'Synthesis of Aminoglycoside-DNA Conjugates', Bioorganic & Medicinal Chemistry Letters 2002 12:1259-1262.
Cutrona et al., "Effects in live cells of a c-*myc* anti-gene PNA linked to a nuclear localization signal", Nature Biotechnology 2000 18:300-303.
Greenberg et al., "Design and Synthesis of New Aminoglycoside Antibiotics Containing Neamine as an Optimal Core Structure:Correlation of Antibiotic Activity with in Vitro Inhibition of Translation", J. Am. Chem. Soc. 1999 121:6527-6541.
Haddad et al., "Design of Novel Antibiotics that bind to the Ribosomal Acyltransfer Site", J. Am. Chem. Soc. 2002 124:3229-3237.
Constantinou-Kokotou et al., "Study of Aminoglycoside-Nucleic Acid Interactions by an HPLC Method", Bioorganic & Medicinal Chemistry Letters 2001 11:1015-1018.
Park et al., "Rapid Combinatorial Synthesis of Aminoglycoside Antibiotic Mimetics: Use of a Polyethylene Glycol-Linked Amine and a Neamine-Derived Aldehyde in Multiple Component Condensation as a Strategy for the Discovery of New Inhibitors of the HIV RNA Rev Responsive Element", J. Am. Chem. Soc. 1996 118:10150-10155.
Sreedhara et al., "Efficient Inorganic Deoxyribonucleases. Greater than 50-Million-Fold Rate Enhancement in Enzyme-Like DNA Cleavage", J. Am. Chem. Soc. 2000 122:8814-8824.
Sreedhara et al., "Novel reagents for targeted cleavage of RNA sequences:towards a new family of inorganic pharmaceuticals", Chem. Commun. 1999 1147-1148.
Verheijen et al., "Efficient Hydrolysis of RNA by a PNA-Diethylenetriamine Adduct", Angew. Chem. Int. Ed. 2000 39(2) : 369-372.
Whitney et al., "Site-specific cleavage of human telomerase RNA using PNA-neocuproine.Zn(II) derivatives", Chem. Commun. 2003 36-37.
Zhou et al., "Novel Binding and Efficient Cellular Uptake of Guanidine-Based Peptide Nucleic Acids (GPNA)", J. Am. Chem. Soc. 2003 125:6878-6879.

* cited by examiner

*Primary Examiner*—Jeffrey E Russel
(74) *Attorney, Agent, or Firm*—Licata & Tyrrell P.C.

(57) ABSTRACT

The present invention relates to methods and compositions pertaining to conjugates composed of a peptide nucleic acid (PNA) moiety and a neamine derivative moiety. Methods for using such conjugates for modulating the activity of a target nucleic acid molecule and for preventing or treating a disease associated with an aberrant nucleic acid molecule are also provided.

4 Claims, No Drawings

PNA-NEAMINE CONJUGATES AND METHODS FOR PRODUCING AND USING THE SAME

INTRODUCTION

This invention was made in the course of research sponsored by the National Institutes of Health (Grant No. AI42520). The U.S. government may have certain rights in this invention.

BACKGROUND OF THE INVENTION

Oligonucleotide analogs are useful as tools in molecular biology, as diagnostics, and as potential therapeutic agents. Peptide nucleic acids (PNAs) are DNA analogs that have received a lot of attention in regard to their high affinity for complementary sequences on RNA and DNA both in a single and double stranded forms (Nielsen, et al. (1991) *Science* 254:1497-1500; Hyrup and Nielsen (1996) *Bioorg. Med. Chem.* 4:5-23; Uhlmann, et al. (1998) *Angew. Chem. Int. Ed.* 37:2796-2823). Their therapeutic potential for gene-specific, nontoxic, and non-immunogenic therapy has been limited as nucleic acid binding agents due to poor uptake into mammalian cells (Koppelhus and Nielsen (2003) *Adv. Drug Deliv. Rev.* 55:267-280). The synthesis of modified PNA or PNA conjugates presents new means of improving the cellular uptake and developing artificial chemical nucleases. For example, PNAs conjugated to diethylenetriamine and neocuproine Zn(II) derivatives are able to hydrolyze RNA targets in vitro (Verheijen, et al. (2000) *Angew. Chem. Int. Ed.* 39:369-372; Whitney, et al. (2003) *S. Chem. Commun.* 1:36-37).

In vivo studies using microinjection (Hanvey, et al. (1992) *Science* 258:1481-1485) and carrier peptides (Cutrona, et al. (2000) *Nature Biotech.* 18:300-303) or guanidine-based PNA (Zhou, et al. (2003) *J. Am. Chem. Soc.* 125:6878-6879) have been described. A membrane-permeating peptide conjugated to a PNA targeting the transactivation response element (TAR) of HIV-1 has been shown to inhibit HIV-1 production when supplemented in HIV-1 infected cell culture (Kaushik, et al. (2002) *J. Virol.* 76:3881-3891).

Aminoglycoside antibiotics such as neomycin B bind specifically to 16S bacterial ribosomal RNA (rRNA) and perturb protein synthesis (Koppelhus and Nielsen (2003) supra). Neomycin also binds to the HIV RNA recognition elements, RRE (Rev Responsive Element).(Zapp, et al. (1993) *Cell* 74:969-978) and TAR (Mei, et al. (1995) *Bioorg. Med. Chem. Lett.* 5:2755-2760) and blocks in vitro the HIV-Rev and HIV-Tat RNA-protein interactions necessary for transactivation. Unfortunately, neomycin B is toxic and high level antibiotic resistance that involves enzymatic modifications have been reported (Mingeot-Leclerc, et al. (1999) *Antimicrob. Agents Chemother.* 43:727-737; Mingeot-Leclerc and Tulkens (1999) *Antimicrob. Agents Chemother.* 43:1003-1012; Kotra, et al. (2000) *Antimicrob. Agents Chemother.* 44:3249-3256). Detailed comparative biochemical experiments, NMR studies and/or molecular modelling have shown that rings I and II of neomycin-class aminoglycosides, corresponding to the neamine structure, are essential structural elements involved in the specific binding to rRNA (Fourmy, et al. (1998) *J. Mol. Biol.* 277:347-362), RRE (Leclerc and Cedergren (1998) *J. Med. Chem.* 41:175-182) and TAR RNA (Hermann and Westhof (1999) *J. Med. Chem.* 42:1250-1261). New chemistries have been developed to synthesize small antiviral or antibiotic agents from neamine (Greenberg, et al. (1999) *J. Am. Chem. Soc.* 121:6527-6541; Park, et al. (1996) *J. Am. Chem. Soc.* 118:10150-10155). The high affinity of polycationic aminoglycosides to DNA was recently used successfully in oligo-2'-deoxyribonucleotides (ODN) transfection into cells for developing gene therapy (Belmont, et al. (2002) *J. Gene Med.* 4:517-526) and the synthesis of ODN-aminoglycoside conjugates were reported (Charles, et al. (2003) *Bioorg. Med. Chem. Lett.* 13:1607). In vitro, aminoglycosides are able to stabilize nucleic acid triple helices (Arya, et al. (2003) *J. Am. Chem. Soc.* 125:3733-3744) and aminoglycoside-copper (II) complexes are very efficient artificial nucleases which hydrolyze RNA (Sreedhara, et al. (1999) A. Chem. Commun. 1147-1148) or DNA (Sreedhara, et al. (2000) *J. Am. Chem. Soc.* 122:8814-8824).

WO 00/39139 teaches aminoglyoside-arginine conjugates wherein the aminoglycoside antibiotic is preferably kanamycin, gentamycin or neomycin that is conjugated to arginine residues.

Neamine derivatives have been prepared in modifying the amino functions, or the 3'-, the 5- or the 6- hydroxyl function in order to increase the affinity for the RNA targets and/or to induce a resistance to aminoglycoside-modifying enzymes (Kotra, et al. (2000) *Antimicrob. Agents Chemother.* 3249-3256; Kotra and Mobashery (2001) *Curr. Org. Chem.* 5:193-205). Combinatorial chemistry has been used to generate neamine libraries of neomycin B "mimetics" by selective modifications at the 5 position (Park, et al. (1996) *J. Am. Chem. Soc.* 118:10150-10155; Greenberg, et al. (1999) *J. Am. Chem. Soc.* 121:6527-6541; Sucheck, et al. (2000) *Angew. Chem. Int. Ed.* 39:1080-1084; Sucheck, et al. (2000) *J. Am. Chem. Soc.* 122:5230-5231). Dimers of neamine have been obtained in which the two subunits are linked by an amino chain attached at the 5-positions such they target rRNA and inhibit resistance causing enzymes (Sucheck, et al. (2000) supra). Aminoglycosides and neamine have also been modified in order to decrease the strength of their electrostatic interactions with aminoglycoside 3'-phosphotransferases types Ia and IIa, responsible for the resistance (Roestamadjli, et al. (1995) *J. Am. Chem. Soc.* 117:80-84; Roestamadjli, et al. (1995) *J. Am. Chem. Soc.* 117:11060-11069; Roestamadjli and Mobashery (1998) *Bioorg. Med. Chem. Lett.* 8:3483-3488; Liu, et al. (2000) *J. Org. Chem.* 65:7422-7431). Neamine derivatives possessing an amino side chain at the 6-position have been synthesised and some of these compounds are very poor substrates for two important purified resistance enzymes while exhibiting interesting antibiotic properties (Haddad, et al. (2002) *J. Am. Chem. Soc.* 124:3229-3237).

SUMMARY OF THE INVENTION

One aspect of the present invention is a composition for modulating the activity of a nucleic acid molecule. Said composition is composed of a peptide nucleic acid moiety conjugated to a neamine moiety, wherein said conjugate is of Formula I.

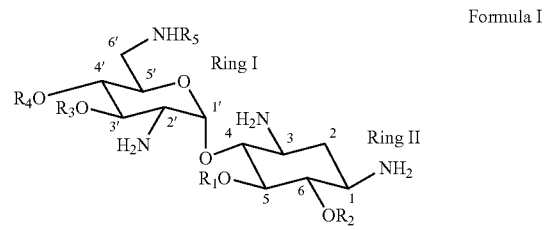

Formula I wherein, at least one of $R_1$, $R_2$, $R_3$, or $R_4$ is a peptide nucleic acid which hybridizes with one or more nucleic acid molecules and the remaining substituents, $R_1$, $R_2$, $R_3$, $R_4$, and $R_5$, are each independently a hydrogen, a neamine, a lipophilic chain, a reactive or catalytic group, or a binding element.

A second aspect of the present invention is a method for producing a peptide nucleic acid-neamine conjugate of Formula I. The method involves the steps of protecting amino functions of the neamine moiety with an acid labile protecting group; protecting hydroxyl functions of the neamine moiety with a protecting group which produces an acid labile ether; conjugating $R_1$, $R_2$, $R_3$, $R_4$, or $R_5$ substituents to the neamine moiety, wherein at least one of $R_1$, $R_2$, $R_3$, or $R_4$ is a PNA which hybridizes with one or more nucleic acid molecules; and deprotecting the amino and hydroxyl functions and recovering the PNA-neamine conjugate.

A further aspect of the present invention is a method for modulating the activity of a nucleic acid molecule. The method involves contacting one or more nucleic acid molecules with a peptide nucleic acid-neamine conjugate of of Formula I which hybridizes with at least one nucleic acid molecule of the one or more nucleic acid molecule so that the function of the at least one nucleic acid molecule is modulated.

A still further aspect of the present invention is a method for preventing or treating a disease associated with an aberrant nucleic acid molecule. This method involves administering to a patient with a disease associated with an aberrant nucleic acid molecule an effective amount of a peptide nucleic acid-neamine conjugate of Formula I which hybridizes with the aberrant nucleic acid molecule so that the function of the aberrant nucleic acid molecule is modulated and the disease associated with said aberrant nucleic acid molecule is prevented or treated.

DETAILED DESCRIPTION OF THE INVENTION

The present invention relates to methods and compositions pertaining to conjugates composed of a peptide nucleic acid (PNA) moiety and a neamine moiety, herein referred to as a PNA-neamine conjugate or neamine-PNA conjugate. A neamine moiety is intended to include a derivative, analog, enantiomer, isomer or tautomer of neamine, as well as any derivative of neamine that retains the biological activity of the parent compound. PNA-neamine conjugates of the present invention are useful in modulating the activity of a target nucleic acid molecule by inactivating or cleaving said nucleic acid molecule and are advantageously used over conjugates known in the art as the neamine moiety facilitates cellular uptake of the PNA, enhances targeting of the PNA component to its complementary target nucleic acid molecule and also exhibits cleaving activity. It is contemplated that, as neamine has four amino functions which are partially ionized at physiological pH, the protonated amino functions interact with the phosphate backbone of a nearby nucleic acid sequence while another unprotonated amino function nucleophylically attacks the same phosphate resulting in cleavage. Further, aminoglycosides are able to stabilize nucleic acid triple helices (Arya, et al. (2003) supra) and aminoglycoside-copper (II) complexes are very efficient artificial nucleases which hydrolyze RNA (Sreedhara, et al. (1999) supra) or DNA (Sreedhara, et al. (2000) supra). Accordingly, the catalytic activity of a PNA-neamine conjugate of the invention is applicable in the cleavage of any nucleic acid molecule including DNA (e.g., genomic DNA, plasmid DNA, cDNAs, and the like) and RNA (e.g., messenger RNA of a specific gene of interest, ribosomal RNA, genomic RNA of pathogenic viruses, telomeric RNA at the end of chromosomes, and the like). Preferably, a PNA-neamine conjugate targets an RNA molecule.

Accordingly, one aspect of the present invention concerns a PNA-neamine conjugate of Formula I.

Formula I

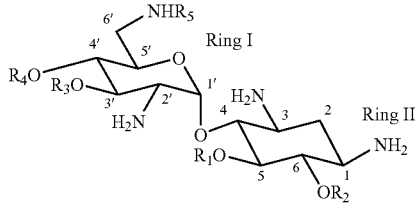

wherein, preferably at least one of $R_1$, $R_2$, $R_3$, or $R_4$ is a peptide nucleic acid and the remaining substituents, $R_1$, $R_2$, $R_3$, $R_4$, and $R_5$, may each independently be a hydrogen; a neamine; a lipophilic chain for enhanced cellular uptake; a reactive and/or catalytic group, for example a metal ion complex, a phenanthroline ring, or imidazole, including, but not limited to, an amino acid (e.g., histidine) or a peptide; a binding element such as an amino group, guanidinium group or a nucleoside base (e.g., adenine, cytosine); a flavin and the like. More preferably, at least one of $R_1$ or $R_4$ is a peptide nucleic acid. While it is preferable that the PNA be attached to a hydroxyl function of the neamine moiety, a PNA may also be attached to the neamine moiety via an amino group (e.g., 1-, 3-, 2'- or 6' groups).

Exemplary compounds comprising the structure of Formula I which depict various substituent R groups and to which a PNA may be conjugated include, but are not limited to, the following:

Compound 1

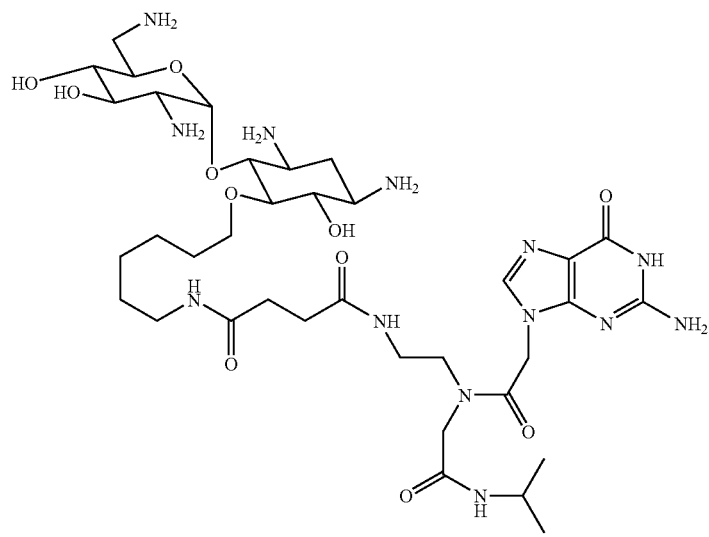

Compound 2
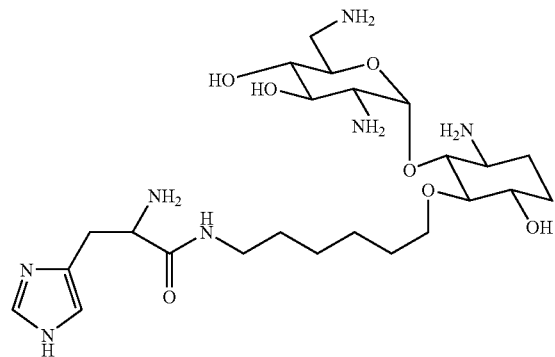
Compound 3
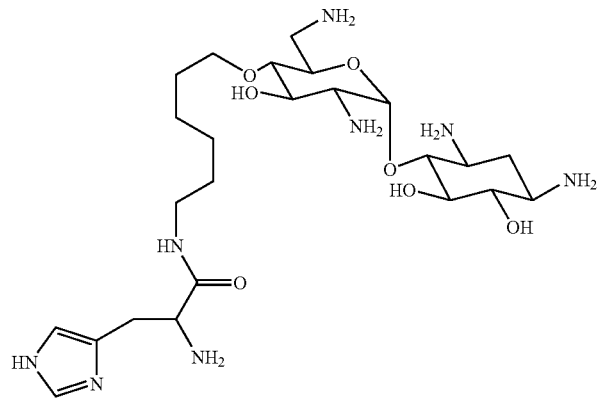
Compound 4
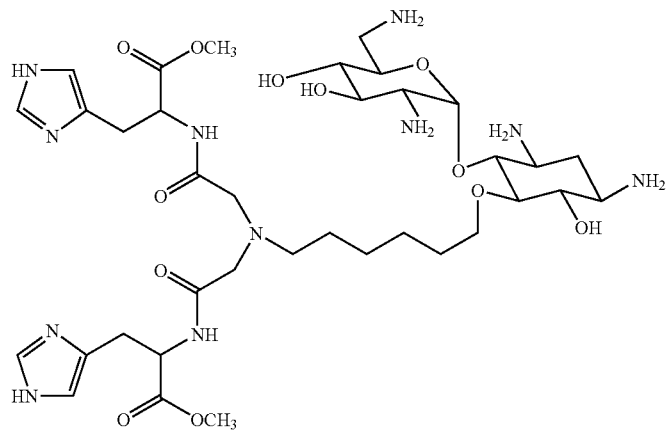
Compound 5
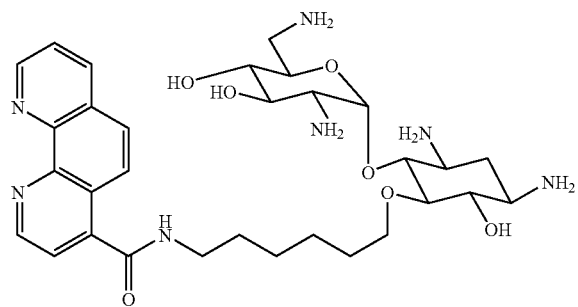

-continued
Compound 6
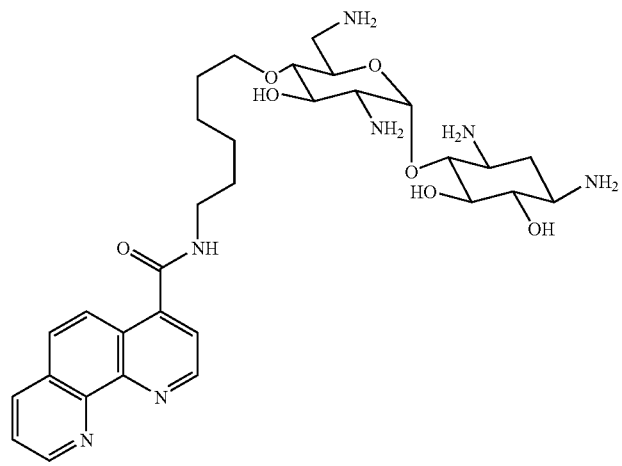
Compound 7
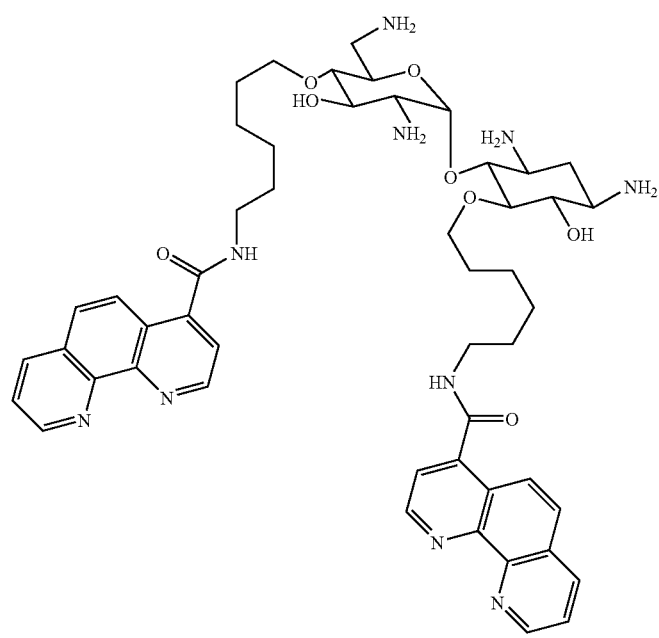
Compound 8
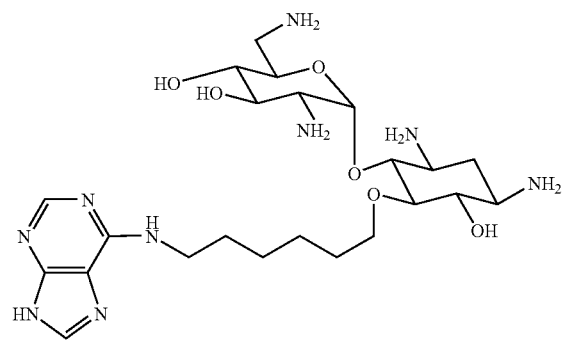
Compound 9
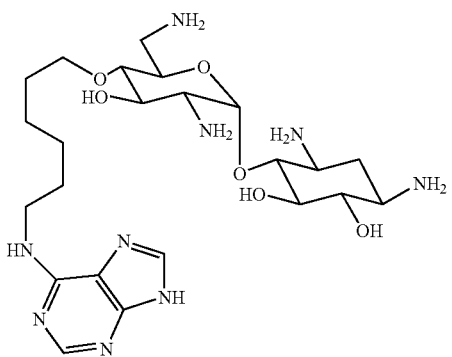

-continued
Compound 10
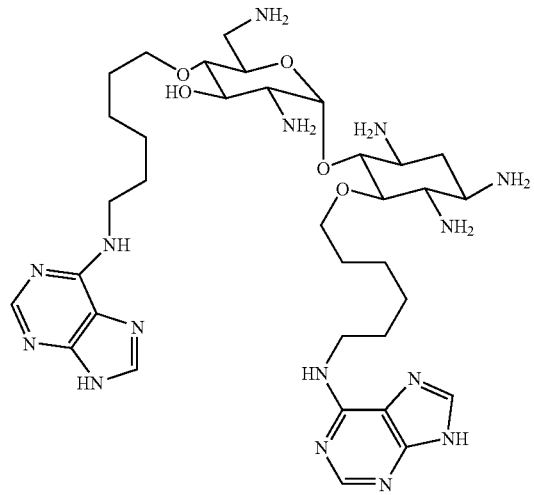
Compound 11
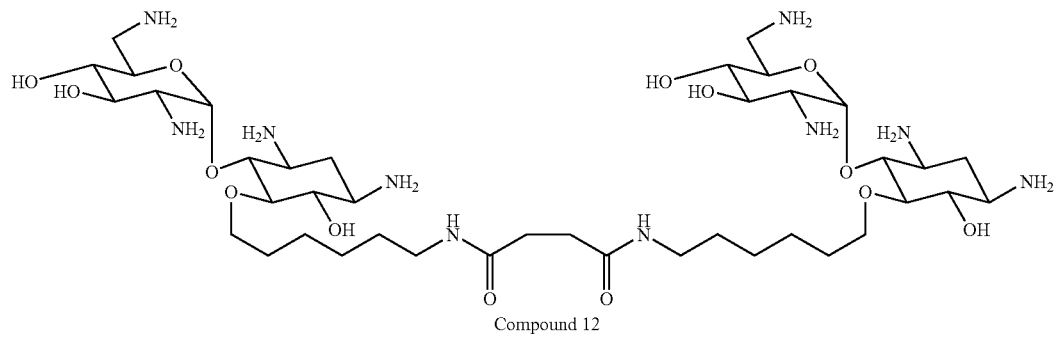
Compound 12
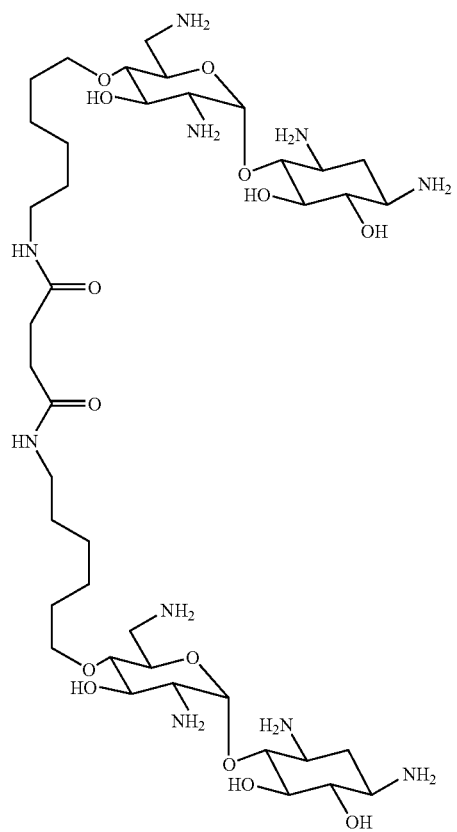
Compound 13
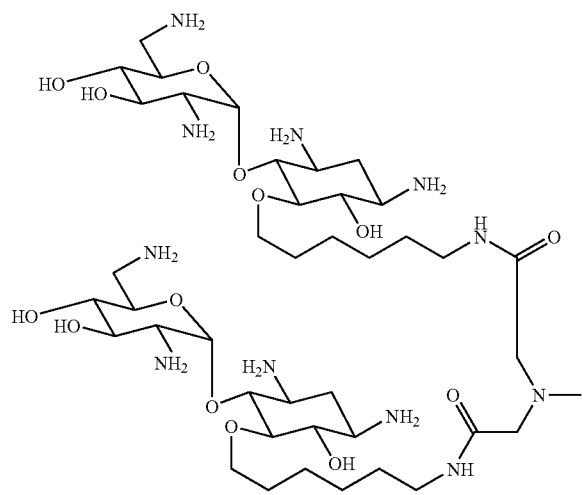

-continued

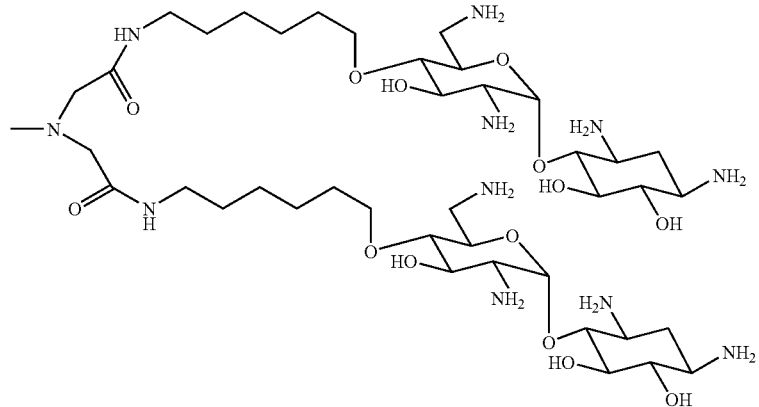
Compound 14

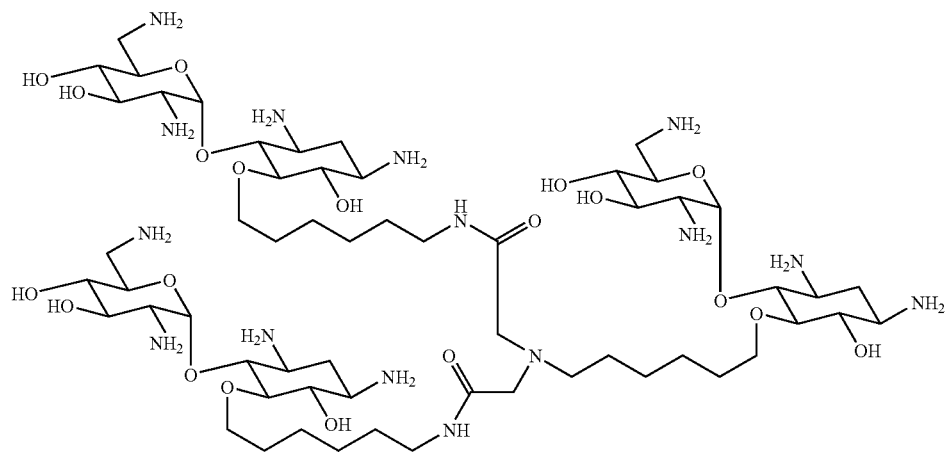
Compound 15

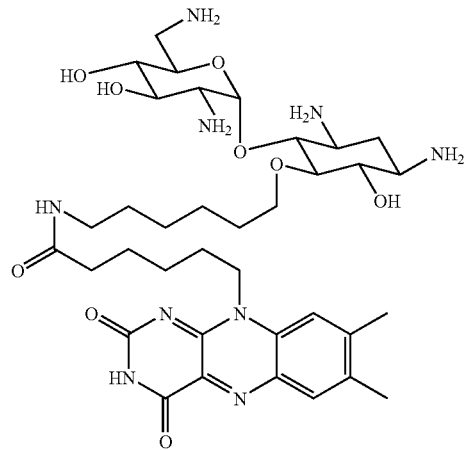
Compound 16

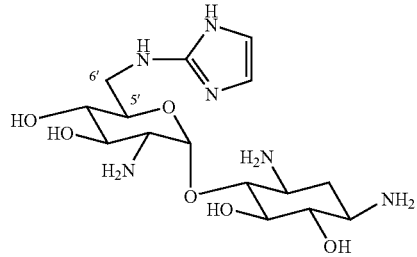
Compound 17

Further compounds of Formula I which exemplify substituent R groups and to which a PNA may be conjugated are provided herein.

Compound 15 depicts an exemplary neamine trimer of the invention (i.e., three neamine moieties linked via the 5 position on Ring I); however, it is contemplated that other trimers may also be prepared (e.g., two neamine moieties linked via the 5 position and one via the 4' position; two neamine moieties linked via the 4' position and one via the 5 position; or three neamine moieties linked via the 4' position). Conjugating neamine dimers or trimers to a PNA may increase the charge or density of a PNA-neamine conjugate to enhance cleavage or cellular uptake. Neamine trimers or dimers may be coupled prior to or after conjugation to the PNA and each neamine moiety may be conjugated to a PNA. Thus, it is contemplated that neamine dimers and trimers may be used to generate mono-, bi- or tri-functional PNA-neamine conjugates which recognize 1, 2 or 3 different target nucleic acid molecules. For example, a neamine dimer of compound 13 may be generated wherein the 4' position of each monomer has the same or two distinct PNA moieties attached.

Moreover, derivatives of neamine including gentamicin, kanamycin, tobramycin, and amikacin may also be conjugated to a PNA to generate a PNA-neamine conjugate of the invention. Preferably, such aminoglycoside derivatives of neamine lack a ribosyl moiety as said ribosyl may destabilize the neamine moiety under the acidic synthesis conditions disclosed herein. As will be evident, one of skill in the art may envision that numerous neamine derivatives may be generated in accordance with the invention.

The PNA moiety of the PNA-neamine conjugate may be any oligomer which can hybridize to an nucleic acid molecule of interest (i.e., a target nucleic acid molecule). The nucleic acid molecule of interest may, for example, be a DNA, an mRNA, pre-mRNA, genomic RNA, or rRNA. The specific hybridization of a PNA oligomer with its target nucleic acid molecule interferes with the normal function of the nucleic acid molecule which may be further facilitated by cleavage by the neamine moiety. Preferably, the target nucleic acid molecule is an aberrant nucleic acid molecule which is deleterious to the cell. For example, an aberrant nucleic acid molecule may include the genomic RNA or DNA or mRNA of an infectious agent, a defectively spliced mRNA, or an RNA which is overexpressed and results in a disease state. The functions of a nucleic acid molecule to be interfered with include all vital functions such as, for example, DNA transcription, translocation of an RNA to the site of protein translation, translation of protein from the RNA, splicing of the RNA to yield one or more mRNA species, and catalytic activity which may be engaged in or facilitated by the RNA. In the context of the present invention, the function of the nucleic acid molecule may be modulated by either increasing (stimulating) or decreasing (inhibiting) its expression or activity; preferably the function of the target nucleic acid molecule is inhibited. By inhibit it is meant that the activity of target nucleic acid molecule or level of nucleic acid molecule is reduced below that observed in the absence of the PNA-neamine conjugates of the instant invention.

It is preferred to target specific nucleic acid molecule with a PNA-neamine conjugate of the invention. Targeting a PNA-neamine conjugate to a particular nucleic acid molecule, in the context of this invention, is a multistep process. The process usually begins with the identification of a nucleic acid sequence whose function is to be modulated. This may be, for example, an mRNA transcribed from a gene whose expression is associated with a particular disorder or disease state or an RNA or DNA from an infectious agent. The targeting process also includes determination of a site or sites within the nucleic acid molecule for the PNA interaction to occur such that the desired effect, e.g., modulation of expression of the protein, will result.

When targeting an mRNA molecule, the PNA may hybridize with the RNA open reading frame (ORF) or coding region, which is known in the art to refer to the region between the translation initiation codon (typically 5'-AUG) and the translation termination codon (typically 5'-UAA, 5'-UAG or 5'-UGA). Other target regions include the 5'-untranslated region (5'-UTR), known in the art to refer to the portion of an mRNA in the 51 ' direction from the translation initiation codon, and thus including nucleotides between the 5' cap site and the translation initiation codon of an mRNA, and the 3'-untranslated region (3'-UTR), known in the art to refer to the portion of an mRNA in the 3' direction from the translation termination codon, and thus including nucleotides between the translation termination codon and 3'-end of an mRNA.

Although some mRNA transcripts are directly translated, many contain one or more regions, known as introns, which are excised from a transcript before it is translated. The remaining (and therefore translated) regions are known as exons and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for PNA compounds targeted, for example, to pre-mRNA.

Once one or more target sites have been identified, oligonucleotides are chosen which are sufficiently complementary to the target, i.e., hybridize sufficiently well and with sufficient specificity, to give the desired effect.

As used herein, hybridization refers to hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligomer is capable of hydrogen bonding with a nucleotide at the same position of a nucleic acid molecule, then the oligomer and the nucleic acid molecule are considered to be complementary to each other at that position. The oligomer and the nucleic acid molecule are complementary to each other when a sufficient number of corresponding positions in each molecule are occupied by nucleotides which can hydrogen bond with each other. Thus, specifically hybridizable and complementary are terms which are used to indicate a sufficient degree of complementarity or precise pairing such that stable and specific binding occurs between the PNA oligomer and the nucleic acid molecule target. It is understood in the art that the sequence of a PNA oligomer need not be 100% complementary to that of its target nucleic acid to be specifically hybridizable. A PNA oligomer is specifically hybridizable when binding of the oligomer to the target nucleic acid molecule interferes with the normal function of the target nucleic acid molecule to cause a loss of utility, and there is a sufficient degree of complementarity to avoid non-specific binding of the PNA oligomer to non-target sequences under conditions in which specific binding is desired, i.e., under physiological conditions in the case of in vivo assays or therapeutic treatment, and in the case of in vitro assays, under conditions in which the assays are performed.

PNA-neamine conjugates of the invention which hybridize to the target and modulate the activity of the target are identified through experimentation, and sequences of exemplary oligomers are provided herein and are well-known to those of skill in the art.

PNA oligomers are commonly used as research reagents and diagnostics. For example, PNA oligomers, which are able to inhibit gene expression with exquisite specificity, are often used by those of ordinary skill to elucidate the function of particular genes.

The specificity and sensitivity of a PNA oligomer is also harnessed by those of skill in the art for therapeutic uses. PNA oligomers have been employed as therapeutic moieties in the prevention and treatment of disease states in animals and man. PNA oligomer drugs have been safely and effectively administered to humans and numerous clinical trials are presently underway. It is thus established that oligomers can be useful therapeutic modalities that can be configured to be useful in treatment regimes for treatment of cells, tissues and animals, especially humans.

A second aspect of the present invention concerns the synthesis of a PNA-neamine conjugate of Formula I. In general, a PNA-neamine conjugate of Formula I may be synthesized by protecting amino functions of the neamine moiety with an acid labile protecting group which may be removed under mild acid conditions; protecting hydroxyl functions of the neamine moiety with a protecting group which yields an acid labile ether; conjugating $R_1$, $R_2$, $R_3$, $R_4$, or $R_5$ substituents to the neamine moiety, wherein at least one of $R_1$, $R_2$, $R_3$, or $R_4$ is a PNA; and deprotecting and recovering the PNA-neamine conjugate.

In the step of protecting amino functions of the neamine moiety, it is preferable to use an acid labile protecting group which may be removed under mild acid conditions. While benzhydryl, trifluoroacetyl, activated sulfonyl groups (activated from one or more substituents), or activated acyl groups may be used in accordance with the synthesis method of the invention, it is most preferable that trityl (e.g., from trityl chloride, 4-monomethoxytrityl, 4,4'-dimethoxytrityl or 4,4', 4"-trimethoxytrityl) or pixyl protecting groups be used. It is contemplated that the step of protecting an amino function is performed in the presence of a base with a pKa higher than the pKas of the neamine amino groups and lower than the pKas of the hydroxyl groups. For example, aliphatic organic bases such as amines (triethylamine, DBU, DABCO, tetrabutylammonium hydroxide, etc.) or mineral bases (potassium hydroxide, etc) are desirable.

The step of protecting hydroxyl functions of the neamine moiety is preferably carried out with a protecting group which yields an acid-labile ether such as a substituted methyl or ethyl ether. Exemplary protecting groups include, but art not limited to, activated benzyl (e.g., methoxy or dimethoxybenzyl), arylmethyl groups (e.g., dimethoxybenzyl, diphenylmethyl, naphtylmethyl, etc.), or substituted methyl or ethyl groups (e.g., alkoxy, pyranyl, furanyl sustituents and the like). In a preferred embodiment, methoxybenzyl groups are used. It is contemplated that the step of protecting a hydroxyl function with is performed in the presence of a base which is able to deprotonate the hydroxyl function. Exemplary bases include, but are not limited to, hydrides, amides (with controlled addition), or hydroxides.

The conditions for carrying out the step of introducing $R_1$, $R_2$, $R_3$, $R_4$, or $R_5$ substituents will vary and will be dependent on the substituent being attached to the neamine. In general, it is preferable that $R_1$, $R_2$, $R_3$, $R_4$, or $R_5$ substituents other than the PNA be attached to the neamine moiety first. For example, a spacer group or arm (e.g., Alkyl(hexyl)amino arms, polyethoxy arms, or amino acid function carrying arms) may be introduced followed by conjugation of the substituent. Exemplary substituents are provided herein. Conditions for conjugating a substituent to a neamine will vary with the substituent and one of skill in the art will know of appropriate conditions for carrying out such conjugations.

In the subsequent attachment of a PNA moiety to the neamine or derivative thereof, the neamine moiety may be attached to any solid support or may be free in solution. For example, when attached to N-terminus of a PNA, the protected "free" neamine derivative is conjugated (e.g., using a coupling reagent used in peptide synthesis) to the PNA that is linked to its solid support of synthesis. Further, in the attachment to the C-terminus of a PNA, the protected neamine derivative may be attached first to a solid support and, subsequently, the PNA is synthesized on this support. The neamine moiety may also be introduced into the PNA sequence from neamine amino acid derivatives such as lysine, aspartic and glutamic acid derivatives.

As used herein, a PNA moiety is, in general, an oligomer preferably comprising from about 8 to about 50 peptide nucleic acid monomers. More preferably, a PNA oligomer comprises from about 12 to about 30 peptide nucleic acid monomers. In general, PNA oligomers have sugar-backbones which are replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539, 082; 5,714,331; and 5,719,262, each of which is herein incorporated by reference. Further teaching of PNA compounds may be found in Nielsen, et al. (1991) *Science* 254: 1497-1500.

Conjugation of a PNA to one or more neamine moieties may occur at the N- and/or the C-terminus of the PNA. Further, one or more identical or different PNA moieties may be utilized. For example, a PNA-neamine conjugate may, in order from N- to C-terminus of the PNA, comprise one of the following combinations: neamine-PNA-neamine$_1$; PNA-neamine, neamine-PNA; PNA-neamine-PNA$_1$-neamine$_1$; neamine-neamine$_1$-PNA, etc.

The steps of deprotecting and recovering the PNA-neamine conjugate, wherein recovery encompasses cleavage from a solid support, are carried out simultaneously in the presence of a mild acid. The acid-labile protecting groups may be removed under conditions used to remove benzhydryloxycarbonyl (Bhoc) protecting groups employed to protect the amino functions of bases during PNA synthesis. Exemplary acids which may be used in accordance with this step of the synthesis method of the invention include, but are not limited to, trifluoroacetic acid, dichloro or trichloroacetic acids, diluted hydrochloric acid, or acetic acid in cases where the protecting groups are more acid sensitive (e.g., when MMT or DMT and dimethoxybenzyl groups are used to protect hydroxyl functions).

In general, the steps of the synthesis method of the present invention may be carried under at a temperature between –10° C. and 100° C., preferably between 0° C. and 50° C., most preferably at about 25° C. Further, it may be desirable that the steps be performed under conditions which avoid moisture (e.g., under argon). Neamine intermediates and final products may be analyzed using standard methodologies such as $^1$H and $^{13}$C NMR, high resolution MS, MS-MS, elemental analysis, IR, TLC, HPLC, and the like to determine purity and structure.

It is contemplated that chiral centers involving a carbon present in a compound of the Formula I may independently of one another have R or S configurations. A compositions of Formula I may contain pure enantiomers or pure diastereomers or mixtures of enantiomers, for example in the form of racemates, or mixtures of diastereomers.

Mixtures of two or more stereoisomers of Formula I are further contemplated with varying ratios of stereoisomers in the mixtures. Compositions of Formula I may also contain trans- or cis-isomers including pure cis-isomers, pure trans-isomers or cis/trans-isomer mixtures with varying ratios of each isomer. When a composition containing a pure compound is desired, diastereomers (e.g., cis/trans-isomers) may be separated into the individual isomers (e.g, by chromatography) or racemates (e.g., separated using standard methods such as chromatography on chiral phases or resolution by crystallization of diastereomeric salts obtained with optically active acids or bases). Stereochemically uniform compositions of Formula I may also be obtained by employing stereochemically uniform reactants or by using stereoselective reactions.

Salts of compounds of Formula I may be obtained using methods well-known to those skilled in the art. For example, a salt may be obtained by combining a compound of the present invention with an inorganic or organic acid or base in a solvent or diluent, or from other salts by cation exchange or anion exchange. As neamine carries amino groups, salts formed from acids are preferred. Salt-forming groups in a compound of Formula I are groups or radicals having basic or acidic properties. Compounds having at least one basic group or at least one basic radical such as a free amino group, a pyrazinyl radical or a pyridyl radical, may form acid addition salts with, for example, inorganic acids such as hydrochloric acid, sulfuric acid, a phosphoric acid, or with suitable organic carboxylic or sulfonic acids. Suitable organic carboxylic or sulfonic acids may include aliphatic mono- or di-carboxylic acids (e.g., trifluoroacetic acid, acetic acid, propionic acid, glycolic acid, succinic acid, maleic acid, fumaric acid, hydroxymaleic acid, malic acid, tartaric acid, citric acid, oxalic acid); amino acids (e.g., arginine, lysine); aromatic carboxylic acids (e.g., benzoic acid, 2-phenoxy-benzoic acid, 2-acetoxy-benzoic acid, salicylic acid, 4-aminosalicylic acid); aromatic aliphatic carboxylic acids (e.g., mandelic acid, cinnamic acid); heteroaromatic carboxylic acids (e.g., nicotinic acid, isonicotinic acid); aliphatic sulfonic acids (e.g., methane-, ethane- or 2-hydroxyethane-sulfonid acid) or aromatic sulfonic acids (e.g., benzene-, p-toluene- or naphthalene-2-sulfonic acid). When several basic groups are present, mono- or poly-acid addition salts may be formed. Compounds of Formula I having acidic groups, e.g., a free carboxy group, may form metal or ammonium salts such as alkali metal or alkaline earth metal salts (e.g., sodium, potassium, magnesium or calcium salts) or ammonium salts with ammonia or suitable organic amines such as tertiary monoamines (e.g., triethylamine or tri-(2-hydroxyethyl)-amine), or heterocyclic bases (e.g., N-ethyl-piperidine or N,N'-dimethylpiperazine).

In the syntheses, purification and identification of the compounds of the present invention, the compounds are typically present in free and salt form, therefore as used herein, a free compound should be understood as including the corresponding salts.

Neamine derivatives, modified with histidine, phenanthroline and adenine at the 4'-position, were efficiently prepared in accordance with the method of the invention.

For modifying neamine at the 5- or 6-position, different protective groups for the amino functions have been used, for example, t-butoxycarbonyl (Roestamadjli, et al. (1995) supra; Roestamadjli, et al. (1995) supra; Roestamadjli and Mobashery (1998) supra; Liu, et al. (2000) supra), benzyloxycarbonyl (Haddad, et al. (2002) supra; Park, et al. (1996) supra) and azido groups (Greenberg, et al. (1999) supra; Sucheck, et al. (2000) supra; Sucheck, et al. (2000) supra). Acetyl (Park, et al. (1996) supra), benzyl (Greenberg, et al. (1999) supra; Sucheck, et al. (2000) supra; Sucheck, et al. (2000) supra) or MOM (Haddad, et al. (2002) supra) groups have been used for protection of the hydroxyl functions.

To prepare 4'-substituted neamine conjugates, protective trityl groups were used for selective protection of two or three hydroxyl functions with 4-methoxybenzyl groups and hexyl arm(s) introduced for the remaining hydroxyl function(s). It was possible to protect the four amino functions with hindered 4-methoxytrityl or trityl groups through the reaction of the corresponding trityl chloride with neamine tetrahydrochloride in triethylamine/DMF at room temperature. Neamine tetrahydrochloride was produced by methanolysis of neomycin B in the presence of hydrochloric acid (82% yield). The trityl derivative 19 was obtained in a 77% yield after chromatography on alumina gel and was characterized by $^{13}$C NMR spectrometry and HRMS. For instance, the four signals corresponding to the carbon atoms carrying three phenyl groups and attached to a nitrogen atom in the trityl groups were detected at 71.0, 70.6, 70.5 and 69.6 ppm, respectively.

The presence of the trityl groups confers to the neamine derivative 19 a high solubility in low polarity 30 organic solvents ($CH_2Cl_2$, THF) which was useful in the next steps.

The poor reactivity of the 5-hydroxyl function in neamine derivatives in which the amino groups are protected with Boc or Cbz groups was overcome by selectivity in a benzylation step (Roestamadjli, et al. (1995) supra; Roestamadjli, et al. (1995) supra; Roestamadjli and Mobashery (1998) supra; Liu, et al. (2000) supra; Haddad, et al. (2002) supra; Park, et al. (1996) supra). Thus, the reactivity of compound 19 with benzyl bromide or 4-methoxybenzyl chloride in the presence of an excess of sodium hydride was used. Though the chemistry developed with 4-methoxybenzyl chloride is described herein, similar results were obtained with benzyl bromide; however, under different conditions, it was not possible to debenzylate the benzyl analogs of the 4-methoxybenzyl derivatives 20 and 21.

The reaction of the tetratritylated derivative 19 in DMF with three equivalents of 4-methoxybenzyl chloride in the presence of NaH and tetrabutylammonium iodide at room temperature gave three main products (HPLC) isolated after chromatography on alumina gel.

The major product obtained in a 45% yield was characterized by NMR spectrometry and HRMS as the tribenzylated derivative 20 (Scheme 1, tetra-N-trityl-tri-O-3', 4',6-(4-methoxybenzyl) derivative). As has been reported (Kotra, et al. (2000) supra; Kotra and Mobashery (2001) supra; Roestamadjli, et al. (1995) supra; Roestamadjli, et al. (1995) supra; Roestamadjli and Mobashery (1998) supra; Liu, et al. (2000) supra; Haddad, et al. (2002) supra; Park, et al. (1996) supra), the 5-hydroxyl function is probably less reactive than the 3',4' and 6-hydroxyl functions due to steric effects. The remaining free hydroxyl function in the isolated tribenzylated derivative 20 was used for preparing a first series of conjugates. Its location at the 5-position was confirmed by NMR experiments on the deprotected derivatives 25, 44-46 and 55 prepared from compound 20. From this derivative, monoconjugates in which the linking chain is attached at a position different from the 5-position may be prepared and, also, diconjugates may be synthesized.

SCHEME 1

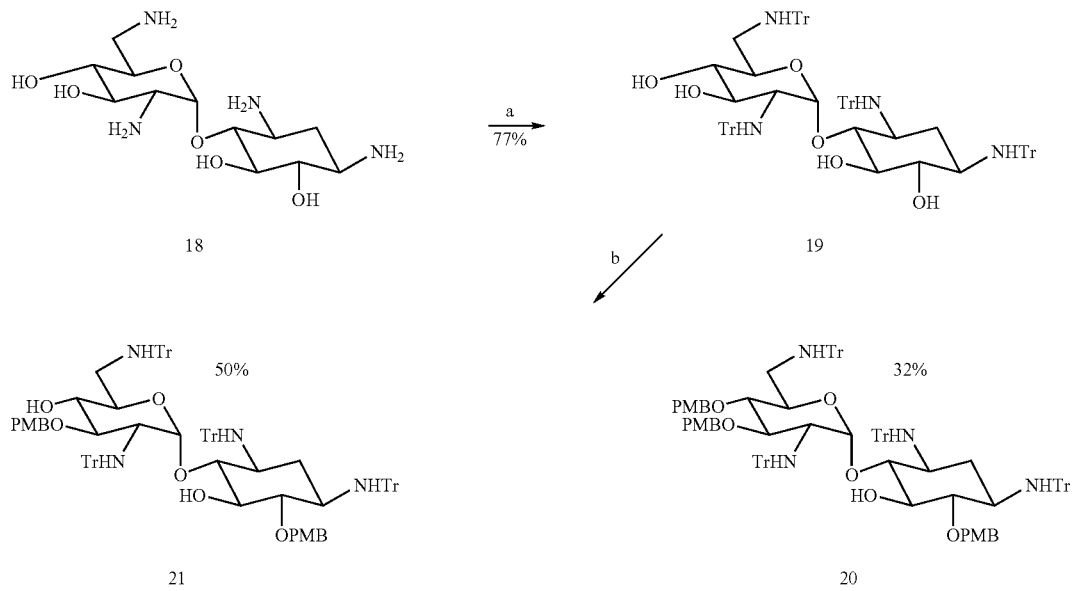

(a) TrCl, Et₃N, DMF, rt; (b) PMBCl, NaH, TBAI, THF or THF/DMF 90:10, rt.

For synthesizing conjugates in which the linking arm is attached at a position different from the 5'-position and obtaining dibenzylated derivative(s), the velocity of the O-benzylation was decreased in a THF/DMF mixture (90:10). The reaction was conducted with 2.5 equivalents of 4-methoxybenzyl chloride or benzyl bromide in the presence of an excess of sodium hydride and tetrabutylammonium iodide at room temperature. HPLC analysis revealed that only one dibenzyl derivatives was formed under these conditions. Formation of the tribenzyl derivative 20 always was observed under different conditions (one addition of the benzyl halide or addition by part). This derivative 20 and the dibenzylated derivative 21 (Scheme 1) were easily isolated after chromatography on alumina gel in 32 and 50% yields, respectively.

$^{13}$C NMR spectrometry confirmed the presence of only one dibenzylated derivative 21. For instance, the signals corresponding to the methylene groups in the two 4-methoxylbenzyl groups were detected at 75.6 and 73.7 ppm, respectively. From this compound, the deprotected amino derivatives 29 and the conjugates 47, 48 and 57 resulting from selective alkylation of one hydroxyl group were prepared. Their structures were determined by NMR spectrometry to assign the structure 21 to the starting dibenzylated derivative (tetra-N-trityl-di-O-3',6-(4-methoxybenzyl) derivative.

For preparing neamine conjugates from the protected trityl tri(methoxybenzylated) and trityl di(methoxybenzylated) neamine derivatives 20 and 21, respectively, compounds 24, 28, 32, possessing one or two flexible n-hexyl arms introduced from the free hydroxyl functions and bearing terminal amino function(s) were synthesized. Their synthesis involved three steps: (1) introduction of one or two bromohexyl chains (synthesis of compounds 22, 26 and 30), (2) substution of the bromine atom(s) for azido group(s) for obtaining compounds 23, 27, 29 and (3) reduction of the azido groups to amino functions. These highly functionalized intermediates were characterized by HMRS and, then, the corresponding deprotected amines were characterized by NMR spectrometry and HMRS.

The bromo derivatives 28, 30, 32 were prepared by reaction of compounds 20 and 21 with 1,6-dibromohexane in the presence of sodium hydride in DMF at 50° C. Using an excess of alkylating reagent (5 equivalents) and of NaH, the tri (methoxybenzylated) derivative 20 gave the 5-bromohexyl derivative 22 in a 76% yield after chromatography on alumina (Scheme 2).

SCHEME 2

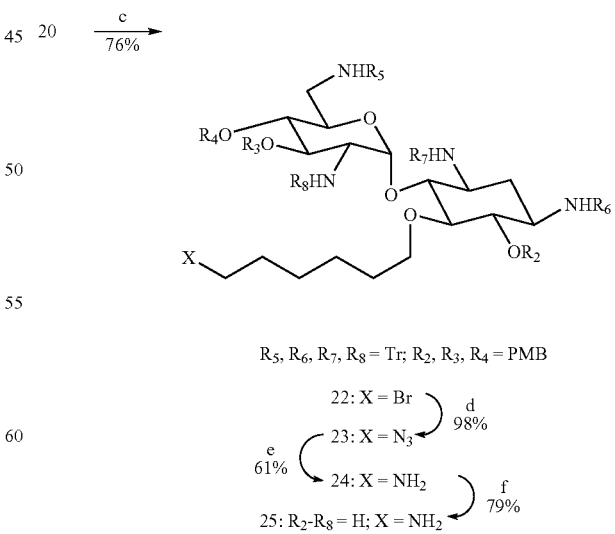

$R_5, R_6, R_7, R_8 = Tr; R_2, R_3, R_4 = PMB$

22: X = Br
23: X = N₃
24: X = NH₂
25: R₂-R₈ = H; X = NH₂

(c) 1,6-dibromohexane (5 equiv.), NaH, DMF, 50° C.; (d) NaN₃, DMF, rt;
(e) triphenylphosphine, H₂O, THF, rt; (f) TFA, anisole, rt.

Under different conditions of reaction, formation of the neamine dimer was not observed. Alkylation of the 3', 6-di (methoxybenzylated) derivative 21 in DMF at 50° C. in the presence of 1.5 equivalents of 1,6-dibromohexane led to the 4'-monobromohexyl derivative 26 isolated in a 60% yield after chromatography (Scheme 3). The reaction selectivity may be explained by the low reactivity of the 5-hydroxyl function (steric effects) (Roestamadjli, et al. (1995) supra; Roestamadjli, et al. (1995) supra; Roestamadjli and Mobashery (1998) supra; Liu, et al. (2000) supra; Haddad, et al. (2002) supra; Park, et al. (1996) supra).

The position of the introduced hexyl arm was determined from the $^{13}$C NMR spectra in comparison to neamine (Table 1).

TABLE 1

| | Neamine | 5-Derivative 25 | | 4'-Derivative 29 | |
|---|---|---|---|---|---|
| | δppm | δppm | Δ δppm/neamine | δppm | Δ δppm/neatnine |
| C 3' | 68.1 | 68.2 | 0.1 | 68.3 | 0.2 |
| C 4' | 70.6 | 70.2 | −0.4 | 79.0 | 8.8 |

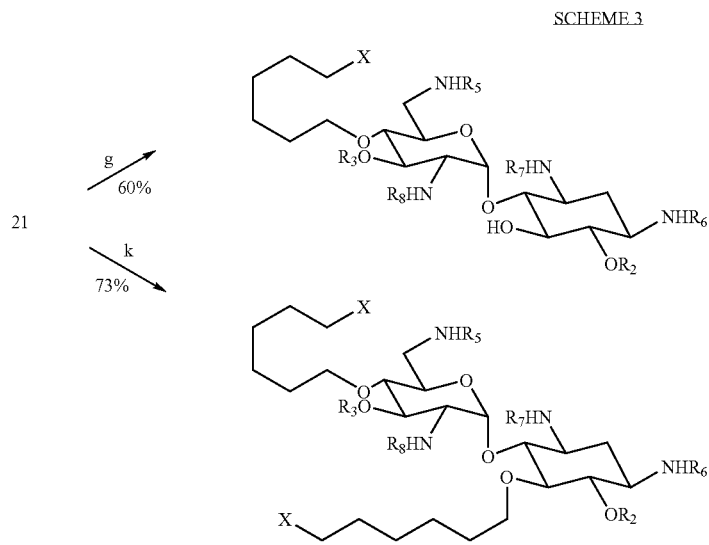

SCHEME 3

$R_5, R_6, R_7, R_8 = Tr; R_2, R_3 = PMB$

26: X = Br
27: X = N$_3$
28: X = NH$_2$
29: R$_2$-R$_8$ = H; X = NH$_2$

30: X = Br
31: X = N$_3$
32: X = NH$_2$
33: R$_2$-R$_8$ = H; X = NH$_2$ (g) 1,6-dibromohexane (1.5 equiv.), NaH, DMF, 50° C.; (h) NaN$_3$, DMF, rt; (i) triphenylphosphine, H$_2$O, THF, rt; (j) TFA, anisole, rt; (k) 1,6-dibromohexane (10 equiv.), NaH, DMF, 50° C.

The 4',5-dibromohexyl derivative 30 was also prepared from compound 21 in a 73% yield in increasing the 1,6-dibromohexane excess (10 equivalents) and the reaction time (Scheme 3).

In order to substitute the terminal bromine atom for an amino group, compounds 22, 26 and 30 were transformed to the corresponding azido derivative 23, 27 and 31, in high yields (93 to 98%, respectively) through reaction with sodium azide in excess in DMF (Schemes 2 and 3). Reduction of the azido group with triphenylphosphine in THF/H$_2$O gave, after chromatography on alumina, the corresponding amino derivatives 24, 28 and 32, respectively (61 to 75% yields).

The amino derivatives 24, 28, 32 were deprotected in a mixture TFA/anisole at room temperature. The corresponding amines 25, 29, 33 (Schemes 2 and 3) were purified by chromatography on C18 reversed phase eluting with water and, then, were passed through an ion exchange resin column (ammonium carboxylate form). They were finally isolated as hydrochloride salts which were characterized by NMR spectrometry (D$_2$O) and HRMS.

TABLE 1-continued

| | Neamine | 5-Derivative 25 | | 4'-Derivative 29 | |
|---|---|---|---|---|---|
| | δppm | δppm | Δ δppm/neamine | δppm | Δ δppm/neatnine |
| C 5' | 69.1 | 69.9 | 0.8 | 68.7 | −0.4 |
| C 4 | 77.4 | 73.1 | −4.3 | 77.2 | −0.2 |
| C 5 | 75.1 | 82.5 | 7.4 | 75.2 | 0.1 |
| C 6 | 72.4 | 72.6 | 0.2 | 72.5 | 0.1 |

Attachment of the linking chain at the 5-position in the amino derivative 25 was confirmed by a strong deshielding effect (≈7.5 ppm) observed for the carbon atom 5 in comparison to neamine and to the amino derivative 29. The shifts (Δδ) measured for the C3' and the C6 signals were not higher than 0.2 ppm. The chemical shifts of these carbon atoms and of the C4' were close to those described for neomycin (Alper, et al. (1998) J. Am. Chem. Soc. 120:1965-1978).

In the amino derivative 29, only the C4' signal was strongly deshielded (≈9 ppm) in comparison to neamine and to the 5-amino derivative 25. This effect revealed that the linking chain was attached at the 4'-position. As a consequence, the two hexyl arms introduced in compound 33 were attached at the 4'- and 5-position. Substituents were attached to the protected amino derivatives 24, 28 and 32.

From starting reagents possessing a carboxylic acid function carrying a bioactive element, conjugates were prepared through peptide bond formation (Scheme 4). The coupling reactions were conducted with 1.5 to 3 equivalents of the carboxylic acid in dichloromethane or DMF at room temperature in the presence of EDC and HOBt as coupling reagents. The conjugates obtained were purified by chromatography on alumina gel.

Three histidine conjugates were synthesized (Scheme 4). Histidine residues are involved in RNA hydrolysis catalyzed by the enzyme ribonuclease A (Deakyne and Allen (1979) *J. Am. Chem. Soc.* 101:3951-3959). Reaction of the amino derivatives 24, 28 and 32 with the protected histidine derivative 34 gave selectively, after treatment with piperidine to remove the Fmoc protecting group, the corresponding conjugates 37, 40 and 42 (Scheme 4).

Copper 1,10-phenanthroline complexes are reported to be able to induce cleavage of DNA or RNA through redox chemistry (Sigman, et al. (1979) *J. Biol. Chem.* 254:12269-12272; Papavassiliou, In: *Methods in Molecular Biology*, Ed G. G. Kneale, Humana Press Inc, Totowa, N.J., 1994, vol 30, pg. 43-77). Copper(II) derivatives of aminoglycosides such as neomycin B are also efficient hydrolytic cleaving agents for cognate RNA motifs (Jezowska-Bojczuk and Bal (1998) *J. Chem. Soc. Dalton Trans.* 153-159; Sreedhara, et al. (1999) *J. Chem. Soc. Chem. Commun.* 1747-1748) and DNA (Sreedhara, et al. (2000) *J. Am. Chem. Soc.* 122:8814-8824).

For preparing the phenanthroline-neamine conjugates 38, 41 and 43 which should cleave the target RNA under different conditions, 4-carboxylic phenanthroline acid 35 and the corresponding amino derivatives 24, 28 and 32 were coupled (Scheme 4).

SCHEME 4

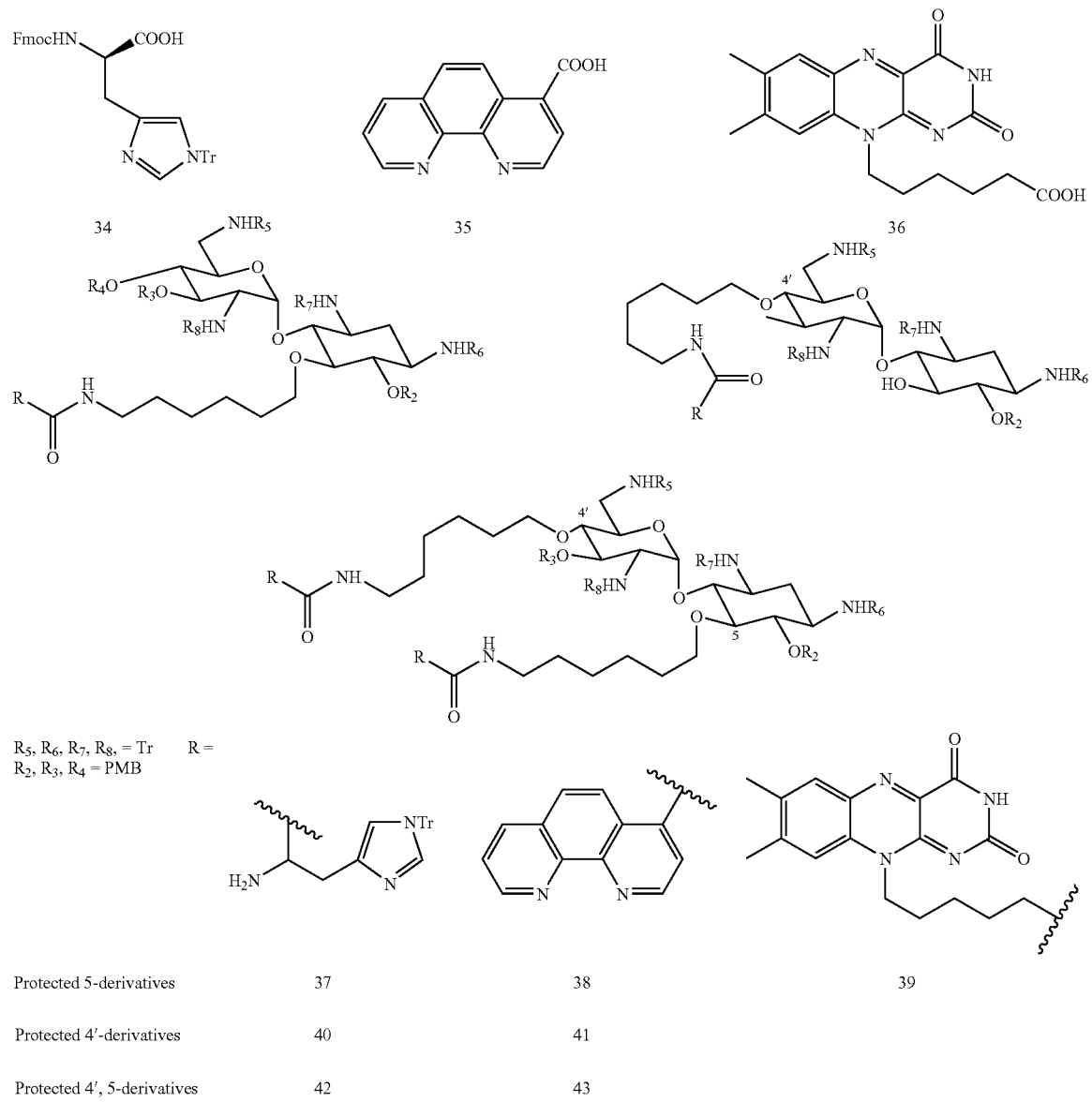

| | | | |
|---|---|---|---|
| $R_2$-$R_8$ = H | R = 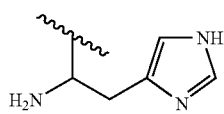 | -continued | |
| Protected 5-conjugates | 44 | 45 | 46 |
| Protected 4'-conjugates | | 47 | 48 |
| Protected 4', 5-conjugates | | 49 | 50 |

As depicted in Scheme 4, the coupling reaction of the neamine derivatives 24, 28 or 32 to compounds 34, 35 or 36 for obtaining the corresponding conjugates 37-43 was conducted in the presence of EDC, HOBt, $CH_2Cl_2$ or DMF at room temperature. The deprotection step which lead to neamine conjugates 44-50 was conducted in the presence of TFA and anisole at room temperature (yields for the two steps were: 58%, 46%, 60%, 59%, 59%, 27%, and 22%, respectively).

The 6-amino modified adenine ring conjugated to the neamine core could interact with the RNA targets and catalyze cleavage reactions. The first crystallographic structure of the ribosome provides the structural basis of the understanding of ribosome activity in peptide bond synthesis (Burgstaller and Famulok (1997) *J. Am. Chem. Soc.* 119:1137-1138). The $N^3$-nitrogen atom of a single adenosine is involved in the catalysis for peptide bond formation within the ribosome.

Reaction of 6-chloropurine in excess with the amino derivative 24, 28 or 32 in ethanol at reflux afforded cleanly the corresponding conjugates 54, 56 and 58 in good yields (75, 73 and 63%, overall yields in conjugates 55, 57 and 59, respectively; Scheme 5).

SCHEME 5

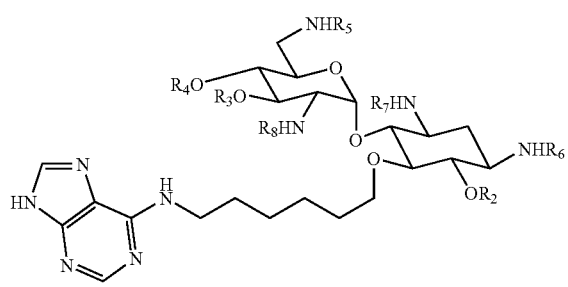

54: $R_5$, $R_6$, $R_7$, $R_8$; $R_2$, $R_3$,
$R_4$ = PMB
55: $R_2$-$R_8$ = H

-continued

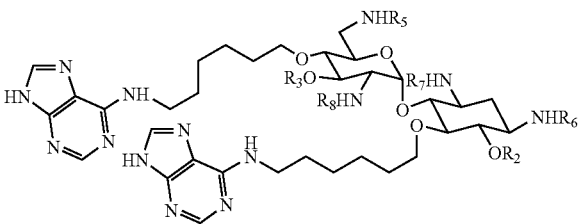

56: $R_5$, $R_6$, $R_7$, $R_8$; $R_2$, $R_3$ = PMB
57: $R_2$-$R_8$ = H

58: $R_5$, $R_6$, $R_7$, $R_8$; $R_2$, $R_3$ = PMB
59: $R_2$-$R_8$ = H

As depicted in Scheme 5, the coupling reaction with 6-chloropurine for obtaining the protected conjugates 54, 56, 58 was conducted in the presence of ethanol, reflux and the deprotection in the presence of TFA and anisole at room temperature.

The conjugates 37-43, 52, 54, and 56 were deprotected in a mixture TFA/anisole at room temperature to lead to the conjugates 44-50 (Scheme 4), 55, 57, 59 (Scheme 5), and 53 (Scheme 6) under the conditions used to prepare the amines 55, 57, 59. The corresponding hydrochloride salts were characterized by NMR spectrometry and HRMS.

SCHEME 6

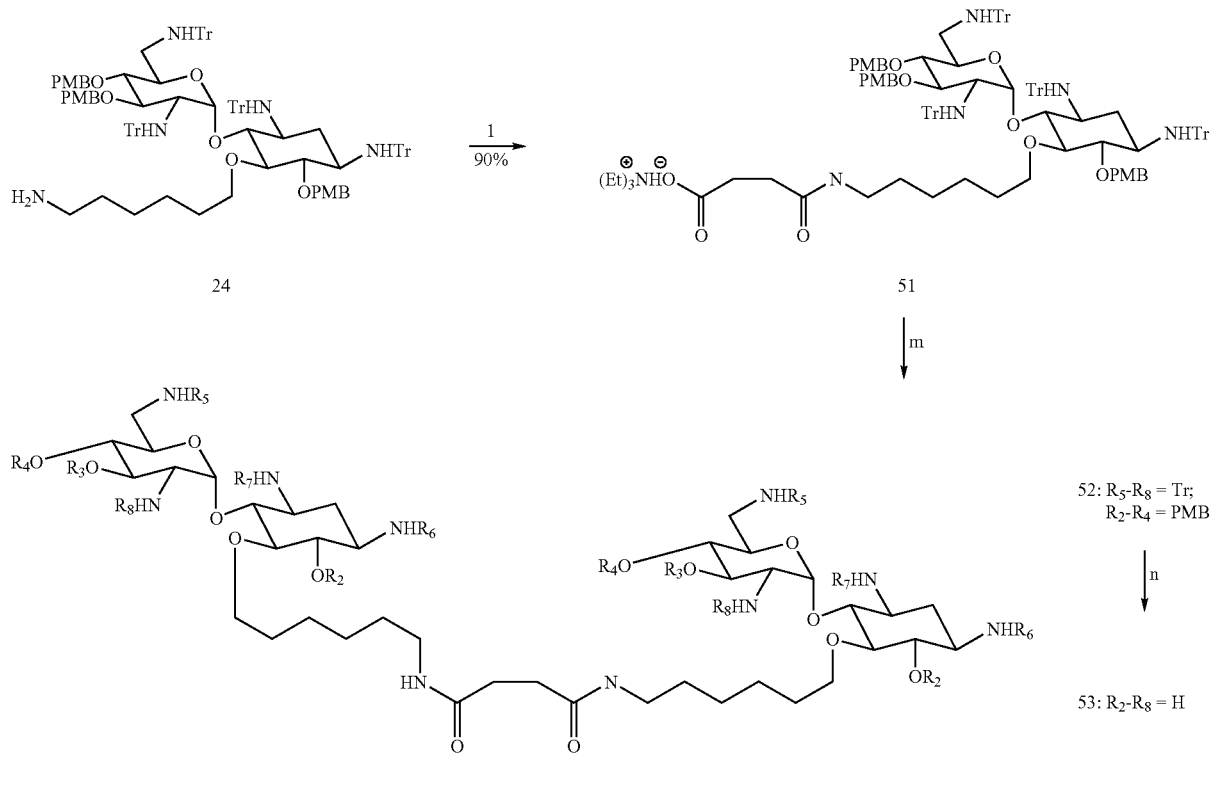

(1) succinic anhydride, Et₃N, CH₂Cl₂; (m) EDC, HOBt, CH₂Cl₂, compound 24, rt; (n) TFA, anisole, rt.

The HMR spectra of these neamine conjugates (electrospray mode) confirmed the previously determined structures. For the conjugates 44-46 and 55 in which the linking chain was attached at the 5-position, ions corresponding to the modified deoxystreptamine core were detected confirming the expected structure. Such ions were also detected from the conjugates 49, 50 and 59 possessing two linking chains. Fragments derived from the aminoglucopyranoside core were not observed.

For the conjugates 47, 48 and 57 in which the linking chain was expected to be attached on the aminoglucopyranoside core (4'-position), no modified deoxystreptamine fragments were observed in the HRMS spectra. This observation confirms that the linking chain was attached on the sugar moiety.

The $^1$H (500 and/or 600 MHz) and $^{13}$C NMR spectra of the conjugates, also confirmed the structures. The chemical shifts observed for the protons and the carbon atoms of the neamine core and the linking chain were close to those of the corresponding amino derivatives (deshielding effects as in Table 1). A NOE correlation was also observed between the anomeric 1'-proton and the methylene protons of the chain attached to the oxygen atom of the neamine core. No NOE correlation was observed between the O—CH$_2$ and the H3', the H5' or the H6' protons.

As a further example of the synthesis and utility of a PNA-neamine conjugate of the invention, an HIV-1 TAR-targeted PNA-neamine conjugate substituted at the 5-position was designed and synthesized and shown to have antiviral activity. This PNA-neamine conjugate of Formula I is represented by compound 60.

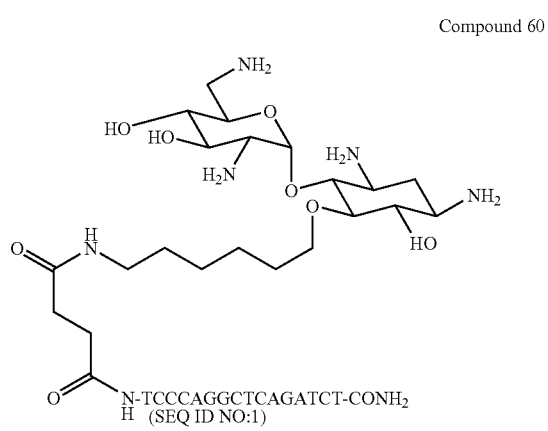

Compound 60

Targeting the TAR element, a nonmutable region of the viral genome in the 5' long terminal repeat (LTR), is one strategy for developing new antiviral agents against drug resistant HIV variants (Kaushik, et al. (2002) supra; Boulmé, et al. (1998) *Nucleic Acid. Res.* 26: 5492-5500; Kaushik, et al.

(2002) *Antiviral Research* 56:13-27; Mayhood, et al. (2000) *Biochemistry* 39:11532-11539).

To determine the activity of the anti-TAR PNA-neamine conjugate 60 to bind with TAR RNA, gel mobility shift assays were performed using $^{32}$P-labeled TAR RNA transcribed from the HIV-1 LTR (Kaushik, et al. (2002) supra; Kaushik, et al. (2002) supra; Mayhood, et al. (2000) supra). A fixed concentration (5 nM) of labelled TAR RNA was used and molar ratios of PNA$_{TAR}$-neamine conjugate 60 to TAR RNA were 0.0, 0.2, 0.5, 0.8, 1.0, 3.0, and 5. A distinct shift in the mobility of TAR RNA was observed due to the formation of specific [PNA-TAR RNA] complexes. This mobility shift was stoichiometric as a complete shift was obtained at 1:1 molar ratio of PNATAR-neamine 60 to TAR RNA.

It was further observed that the anti-TAR PNA-neamine conjugate 60 was also able to block reverse transcription of the HIV-1 TAR catalyzed by the viral enzyme, reverse transcriptase. This has an additional impact on viral replication besides influencing Tat-mediated transactivation.

In the neamine core of the conjugate, the protonated and unprotonated amino functions present at about pH 7 may cooperate to result in cleavage. Thus, the anti-TAR PNA-neamine 60 was incubated with its target RNA at various time points to monitor RNA cleavage. An internally $^{32}$P-labelled HIV-1 TAR RNA was incubated with 3-fold excess of the anti-TAR PNA-neamine conjugate 60 in the absence or presence of 5 mM MgCl$_2$ at 25° C. and pH 7.8 ([RNA]$_0$=10 nM). Reaction products from 1, 5 and 10 hour incubations were analyzed on a denaturing 8% polyacrylamide-urea gel and subjected to phosphorimager analysis. The results of these experiments indicate that and anti-TAR PNA-neamine conjugate 60 is able to induce RNA cleavage upon prolonged incubation. Further, this cleavage activity is strongly inhibited in the presence of 5 mM Mg$^{2+}$.

The ability of a TAR-specific PNA-neamine conjugate to block HIV-1 production when supplemented in the culture medium was also examined. Lymphocyte CEM cells were infected with pseudotyped HIV-1 virions carrying the firefly luciferase reporter gene. The infected cells were incubated with varying concentration of PNA$_{TAR}$-neamine conjugate 60 or naked PNA$_{TAR}$ during 48 hours at 37° C. and lysed to measure firefly luciferase activity. Anti-TAR PNA-transportan conjugate (PNA-membrane-permeating peptide conjugate) known to inhibit HIV-1 replication (Kaushik, et al. (2002) supra) was used as a positive control. Inhibition of luciferase expression was observed at all concentrations of PNATAR-neamine conjugate. Approximately, 50% inhibition was noted at 1 µM concentration of the conjugate. Supplementation of naked PNA of SEQ ID NO:1 in the culture medium had no influence on luciferase gene expression. Unconjugated PNA of SEQ ID NO:1 and a neamine core (Formula I, wherein R$_1$, R$_2$, R$_3$, R$_4$, and R$_5$=H) did not inhibit HIV-1 replication even at concentrations greater than 5 µM in the culture medium.

Accordingly, attachment of a neamine core to the terminal amino function of a PNA targeting a nucleic acid sequence such as the TAR region of the HIV-1 RNA genome, facilitates cellular uptake of the PNA and, as shown herein, results in potent inhibition of viral replication. Such a conjugate also exhibits significant RNA cleavage activity in the absence of magnesium ions. Further, the observed cleavage of TAR RNA appears very efficient as compared to PNA conjugate-based ribonuclease mimics (Verheijen, et al. (2000) supra; Whitney, et al. (2003) supra). Not wishing to be bound to a particular mechanism of action, the observed antiviral activity of the conjugate may have occurred through binding to the target RNA and perturbation of the transactivation process; blockage of viral infection by aborting reverse transcription in the TAR region; or by inducing a cleavage in the TAR region upon binding to the target sequence. These results indicate that aminoglycoside-PNA conjugates may be exploited as potential antiviral and anticancer agents.

Accordingly, a third aspect of the present invention concerns the use of a PNA-neamine conjugate of Formula I for modulating the activity of a target nucleic acid molecule. The method involves contacting one or more nucleic acid molecule with a PNA-neamine conjugate of Formula I so that the PNA-neamine conjugate hybridizes with its complement (i.e., specific binding occurs between the PNA and the nucleic acid target) thereby modulating the activity of the target nucleic acid molecule. Preferably, the target nucleic acid molecule is in a cell, however, a target nucleic acid molecule may be in a cell-free suspension. For example, a viral RNA-specific PNA-neamine conjugate may be used to decontaminate a blood sample suspected of containing a viral contaminant. It is contemplated that the PNA-neamine conjugates of the invention may be targeted to virtually any RNA transcript and, similar to ribozymes, achieve efficient cleavage in vitro (Uhlenbeck (1987) *Nature* 328:596; Haseloff and Gerlach (1988) *Nature* 334:585).

A further aspect of the present invention is a method for preventing or treating a disease associated with an aberrant nucleic acid molecule. The method involves administering a PNA-neamine conjugate of Formula I to a patient with a disease associated with an aberrant nucleic acid molecule an effective amount of a peptide nucleic acid-neamine conjugate of Formula I which hybridizes with the aberrant nucleic acid molecule so that the function of the aberrant nucleic acid molecule is modulated and the disease associated with said aberrant nucleic acid molecule is prevented or treated.

Aberrant nucleic acid molecule targets include, but are not limited to, the HIV-1 genome, mRNA encoding c-myb, c-myc, oct-1, SRF, NF-κB, PDGF receptor, bFGF receptor, angiotensin II, endothelium-derived relaxing factor and the like. Inactivation or cleavage of such nucleic acid molecules will be useful for inhibiting viral replication, inhibiting proliferation of certain cancers associated with elevated levels of RNA transcripts, etc.

Like PNAs (Levett, et al. (2002) *HIV Clin Trials* 3(4):272-8; Robak (2002) *Leuk. Lymphoma* 43(3):537-48), PNA-neamine conjugates of the present invention are useful as therapeutic agents for preventing and treating human disease. However, unlike currently administered PNAs, the PNA-neamine conjugates of the present invention have an enhanced cellular uptake and cleaving activity. The PNA-neamine conjugates may be designed to cleave specific nucleic acid molecule targets within the background of cellular nucleic acids. Such a cleavage event renders the nucleic acid molecule non-functional and may, for example, abrogate protein expression from an RNA. In this manner, synthesis of a protein associated with a disease state may be selectively inhibited.

Use of PNA-neamine conjugates of the invention will lead to better treatment of the disease progression by affording the possibility of combination therapies (e.g., multiple PNA-neamine conjugates targeted to different genes, PNA-neamine conjugates coupled with known small molecule inhibitors, or intermittent treatment with combinations of PNA-neamine conjugates and/or other chemical or biological molecules).

Delivery of PNA-neamine conjugates may include those already known for other antisense and PNA compositions (e.g, Akhtar et al. (1992) *Trends Cell Bio.* 2:139; Delivery Strategies for Antisense Oligonucleotide Therapeutics, ed.

Akhtar, 1995; WO 94/02595). PNA-neamine conjugates may be administered to patients or cells by a variety of methods known to those familiar to the art, including, but not limited to, encapsulation in liposomes, by iontophoresis, or by incorporation into other vehicles, such as hydrogels, cyclodextrins, biodegradable nanocapsules, and bioadhesive microspheres. For some indications, PNA-neamine conjugates may be directly delivered ex vivo to cells or tissues with or without the aforementioned vehicles. Alternatively, the PNA-neamine conjugates/vehicle combination may be locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery and the like.

The PNA-neamine conjugates of the instant invention may be used as pharmaceutical agents. Pharmaceutical agents prevent, inhibit the occurrence, or treat (alleviate a symptom to some extent, preferably all of the symptoms) of a disease state in a patient.

The PNA-neamine conjugates of the invention may be administered and introduced into a patient by any standard means, with or without stabilizers, buffers, and the like, to form a pharmaceutical composition. When it is desired to use a liposome delivery mechanism, standard protocols for formation of liposomes may be followed. The compositions of the present invention may also be formulated and used as tablets, capsules or elixirs for oral administration; suppositories for rectal administration; sterile solutions; suspensions for injectable administration; and the like.

A pharmaceutical composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell. For example, pharmacological compositions injected into the blood stream should be soluble. Other factors are known in the art, and include considerations such as toxicity and forms that prevent the composition or formulation from exerting its effect.

The use of a composition comprising surface-modified liposomes containing poly (ethylene glycol) lipids (PEG-modified, or long-circulating liposomes or stealth liposomes) is also contemplated. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic, et al. (1995) Chem. Rev. 95:2601-2627; Ishiwata et al. (1995) Chem. Pharm. Bull. 43:1005-1011). Such liposomes have been shown to accumulate selectively in tumors, presumably by extravasation and capture in the neovascularized target tissues (Lasic, et al. (1995) Science 267:1275-1276; Oku et al. (1995) Biochim. Biophys. Acta 1238:86-90). The long-circulating liposomes enhance the pharmacokinetics and pharmacodynamics of drugs, particularly compared to conventional cationic liposomes which are known to accumulate in tissues of the MPS (Liu et al. (1995) J. Biol. Chem. 42:24864-24870).

The present invention also includes compositions prepared for storage or administration which include a pharmaceutically effective amount of the desired compounds in a pharmaceutically acceptable carrier or diluent. Such pharmaceutical compositions may be prepared by methods and contain carriers which are well known in the art. A generally recognized compendium of such methods and ingredients is Remington: The Science and Practice of Pharmacy, Alfonso R. Gennaro, editor, 20th ed. Lippingcott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

As used herein, a patient is intended to refer to an organism to which the PNA-neamine conjugates of the invention may be administered. Preferably, a patient is a mammal, e.g., a human, primate, bovine, porcine, dog, cat, or rodent.

A pharmaceutically effective dose or amount is that dose required to prevent, inhibit the occurrence, or treat (alleviate a symptom to some extent, preferably all of the symptoms) of a disease state. The pharmaceutically effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the PNA-neamine conjugate.

The invention is described in greater detail by the following non-limiting examples.

Examples 1-11 describe the synthesis of amino and azido derivatives and neamine conjugates at the 5-position, 4'-position, and 4', 5-positions with histidine, adenine and flavin substituents.

General Procedures. Thin-layer chromatographic data ($R_f$ values) were obtained with Macherey Nagel ALUGRAM® SIL G/UV$_{254}$ analytical sheets (layer: 0.25 mm) developed with dichloromethane-methanol 95:5 ($R_f^A$) or 90:10 ($R_f^B$), pentane-dichloromethane 60:40 ($R_f^C$) or 50:50 ($R_f^D$).

EXAMPLE 1

Protection of Amine Functions; Preparation of Compound 19

A solution of neamine 18 (5.0 g, 10.6 mmol) in DMF/triethylamine (60/8 mL) under Ar was stirred at room temperature for 1 hour and then a solution of trityl chloride (13.6 g, 48.6 mmol) in DMF/triethylamine (130/8 mL) was added. After 4 hour at room temperature, dichloromethane (200 mL) was added. The resulting solution was washed with water (2×250 mL), dried over $Na_2SO_4$ and evaporated. The residue was precipitated in pentane and then chromatographed on alumina gel in $CH_2Cl_2$-methanol (95:5) to lead to tetratritylated derivative 19 (10.6 g, 8.2 mmol, 77%, $R_f^A$ 0.60): mp 178-179° C.; $^{13}$C NMR (50 MHz, $CDCl_3$) δ 146.5-145.7 (CPh), 129.5-125.5 (CHPh), 98.0 (C1'), [82.6, 77.1, 75.6, 73.4, 72.3, 71.6] (6CH nea), [71.0, 70.6, 70.5, 69.6] (4 C (Ph)$_3$), [57.6, 54.2, 52.7] (3CH Nea), 45.2 (C6'), 34.6 (C2); LRMS (FAB$^+$, NBA) m/z=1313 [M+Na]$^+$, 1291 [M+H]$^+$, 1047 [M-Tr+H]$^+$; HRMS (electrospray) Calcd for $C_{88}H_{82}N_4O_6Na$ [M+Na]$^+$: 1313.6132, found: 1313.6139, Calcd for $C_{88}H_{82}N_4O_6K$ [M+K]$^+$: 1329.5872, found: 1329.5811.

EXAMPLE 2

Protection of Hydroxyl Functions; Preparation of Compounds 20 and 21

To a solution of compound 19 (9.0 g, 6.9 mmol) in THF/DMF (90/10 mL) under Ar, sodium hydride (60%, 800 mg, 21 mmol), tetrabutylammonium iodide (2.6 g, 6.9 mmol) and 4-methoxybenzyl chloride (2.4 mL, 17.4 mmol) were added. The mixture was stirred at room temperature for 12 hours, then dichloromethane (200 mL) and a saturated aqueous ammonium chloride solution (150 mL) were added. The organic layer was washed twice with water (200 mL), dried over $Na_2SO_4$ and evaporated. The residue was chromatographed on alumina gel in pentane-$CH_2Cl_2$ (7:3) for obtaining compounds 20 (tribenzylated product, 3.7 g, 2.24 mmol, 32%, $R_f^D$ 0.78) and 21 (dibenzylated product, 5.2 g, 3.4 mmol, 49%, $R_f^D$ 0.31).

Tribenzylated Derivative 20: mp 152-153° C.; $^{13}$C NMR (50 MHz, $CDCl_3$) δ 159.2, 159.0 ($COCH_3$), 147.2-146.1 (CPh), 131.1-125.7 (CHPh), 113.9-113.6 (CH o-$OCH_3$), 94.6 (C1'), [86.0, 81.9, 81.1, 77.1, 76.0, 73.1] (6CH nea), 75.6, 74.5, 73.9 ($BnCH_2$), [71.0, 70.9, 70.5, 70.0] (4C(Ph)$_3$), [58.1, 53.0, 52.7] (3CH nea), 55.2 ($CH_3O$), 45.3 (C6'), 34.6 (C2); LRMS (FAB$^+$, NBA) m/z=1651 [M+H]$^+$, 1674 [M+Na]$^+$, 1047 [M-Tr+H]$^+$; HRMS (electrospray) Calcd for $C_{112}H_{106}N_4O_9Na$ [M+Na]$^+$: 1673.7858, found: 1673.7858, Calcd for $C_{112}H_{106}N_4O_9K$ [M+K]$^+$: 1689.7597, found: 1689.7596.

Dibenzylated Derivative 21. mp 134-135° C.; $^{13}$C NMR (50 MHz, $CDCl_3$) δ 159.1-159.0 ($COCH_3$), 147.0-146.1 (CPh), 131.0-125.7 (CHPh), 113.7 (CH o-$OCH_3$), 95.2 (C1'), [85.6, 81.9, 81.5, 77.2, 76.9] (6CH nea), 75.6, 73.7 ($BnCH_2$), [71.0, 70.6, 70.5, 70.0] (4C(Ph)$_3$), [58.1, 53.0, 52.7] (3CH nea), 55.1 ($CH_3O$), 46.2 (C6'), 35.3 (C2); LRMS (FAB$^+$, NBA) m/z=1553 [M+Na]$^+$, 1289 [M-Tr+H]$^+$; HRMS (electrospray) Calcd for $C_{104}H_{99}N_4O_8$ [M+H]$^+$: 1531.7463, found: 1531.7407, Calcd for $C_{104}H_{99}N_4O_8Na$ [M+Na]$^+$: 1553.7282, found: 1553.7290, Calcd for $C_{104}H_{98}N_4O_8K$ [M+K]$^+$: 1569.7022, found: 1569.7013.

EXAMPLE 3

Synthesis of the Bromo Derivatives 22, 26 and 30.

To a solution of compound 20 or 21 in DMF under Ar, were added successively sodium hydride (60% suspension) and 1,6-dibromohexane. The mixture was stirred for 12 hours at 60° C. After cooling, dichloromethane (200 mL) and then an aqueous saturated ammonium chloride solution (150 mL) were added. The organic layer was washed twice with water (100 mL), dried over $Na_2SO_4$ and evaporated. The residue was chromatographed on alumina gel in pentane-$CH_2Cl_2$ (7:3) to lead to the corresponding bromo derivatives 22, 26 or 30.

Compound 22. Starting neamine derivative 20 (5.0 g, 3.03 mmol), DMF (60 mL), NaH (580 mg, 15.0 mmol), 1,6-dibromohexane (2.33 mL, 15.1 mmol), bromo derivative obtained 22 (4.2 g, 2.31 mmol, 76%, $R_f^C$ 0.54): mp 120-121° C.; LRMS (FAB$^+$, NBA) m/z=1837 [M+Na]$^+$; HRMS (electrospray) Calcd for $C_{118}H_{117}N_4O_9{}^{79}BrNa$ [M+Na]$^+$: 1835.7902, found: 1835.7908, Calcd for $C_{118}H_{117}N_4O_9{}^{79}BrK$ [M+K]$^+$: 1851.7641, found: 1851.7642.

Compound 26. Starting neamine derivative 21 (15.0 g, 9.79 mmol), DMF (150 mL), NaH (980 mg, 24.5 mmol), 1,6-dibromohexane (2.27 mL, 14.7 mmol), bromo derivative obtained 26 (10.0 g, 5.90 mmol, 60%, $R_f^C$ 0.28): mp 91-92° C.; HRMS (electrospray) Calcd for $C_{110}H_{110}N_4O_8{}^{79}Br$ [M+H]$^+$: 1693.7507, found: 1693.7504, Calcd for $C_{110}H_{109}N_4O_8{}^{79}BrNa$ [M+Na]$^+$: 1715.7326, found: 1715.7297.

Compound 30. Starting neamine derivative 21 (6.70 g, 4.37 mmol), DMF (80 mL), NaH (822 mg, 20 mmol), 1,6-dibromohexane (6.74 mL, 43.7 mmol ), bromo derivative obtained 30 (5.60 g, 3.01 mmol, 69%, $R_f^C$ 0.71): mp 112-113° C.; HRMS (electrospray) Calcd for $C_{116}H_{121}N_4O_8{}^{79}Br_2$ [M+H]$^+$: 1855.7551, found: 1855.7566, Calcd for $C_{116}H_{120}N_4O_8{}^{79}Br_2Na$ [M+Na]$^+$: 1877.7371, found: 1877.7380, Calcd for $C_{116}H_{120}N_4O_8{}^{79}Br_2K$ [M+K]$^+$: 1893.7110, found: 1893.7118.

EXAMPLE 4

Synthesis of the Azido Derivatives 23, 27 and 31

To a solution of the bromo derivative 22, 26 or 30 in DMF, was added sodium azide. The mixture was stirred at room temperature for 2 hours and then dichloromethane was added (60 mL). The resulting solution was washed twice with water (50 mL), dried over $Na_2SO_4$ and evaporated. The residue was chromatographed on alumina gel in pentane-$CH_2Cl_2$ (6:4) for obtaining the corresponding azido derivative 23, 27 or 31.

Compound 23. Bromo derivative 22 (2.50 g, 1.37 mmol), DMF (30 mL), $NaN_3$ (447 mg, 6.80 mmol), azido derivative obtained 23 (2.40 g, 1.35 mmol, 98%, $R_f^C$ 0.31): IR ($CH_2Cl_2$): $v_{max}$(cm$^{-1}$) 2095; mp 118-119° C.; HRMS (electrospray) Calcd for $C_{118}H_{117}N_7O_9$ [M+H]$^+$: 1776.8991, found: 1776.8976, Calcd for $C_{118}H_{117}N_7O_9Na$ [M+Na]$^+$: 1798.8810, found: 1798.8721.

Compound 27. Bromo derivative 26 (3.00 g, 1.77 mmol), DMF (30 mL), $NaN_3$ (230 mg, 3.50 mmol), azido derivative obtained 27 (2.80 g, 1.69 mmol, 93%, $R_f^C$ 0.20): IR ($CH_2Cl_2$): $v_{max}$(cm$^{-1}$) 2095; mp 120-121° C.; HRMS (electrospray) Calcd for $C_{110}H_{110}N_7O_8$ [M+H]$^+$: 1656.8415, found:

1656.8407, Calcd for $C_{110}H_{109}N_7O_8Na$ [M+Na]$^+$: 1678.8223, found: 1678.8211.

Compound 31. Bromo derivative 30 (4.00 g, 2.15 mmol), DMF (40 mL), NaN$_3$ (1.40 g, 21.0 mmol), azido derivative obtained 31 (3.60 g, 2.02 mmol, 93%, $R_f^C$ 0.34): IR (CH$_2$Cl$_2$): $\nu_{axm}$(cm$^{-1}$) 2095; mp 117-118° C.; HRMS (electrospray) Calcd for $C_{116}H_{121}N_{10}O_8$ [M+H]$^+$: 1781.9369, found: 1781.9394, Calcd for $C_{116}H_{120}N_{10}O_8Na$ [M+Na]$^+$: 1803.9188, found: 1803.9183, Calcd for $C_{116}H_{120}N_{10}O_8K$ [M+K]$^+$: 1819.8928, found: 1819.8895.

EXAMPLE 5

Synthesis of the Amino Derivatives 24, 28 and 32

To a solution of the azido derivative 23, 27 or 31 in THF/H$_2$O (95/5, 30 mL), triphenylphosphine was added. The solution was refluxed for 3 hours and then evaporated. The residue was chromatographed on alumina gel in CH$_2$Cl$_2$-methanol (98:2 to 95:5) for obtaining the corresponding amino derivative 24, 28 or 32.

Compound 24. Azido derivative 23 (2.20 g, 1.24 mmol), triphenylphosphine (1.62 g, 6.18 mmol), amino derivative obtained 24 (1.30 g, 0.74 mmol, 60%, $R_f^A$ 0.51): mp 120-121 ° C.; HRMS (electrospray) Calcd for $C_{118}H_{120}N_5O_9$ [M+H]$^+$: 1750.9086, found: 1750.9075.

Compound 28. Azido derivative 27 (2.00 g, 1.21 mmol), triphenylphosphine (1.58 g, 6.03 mmol), amino derivative obtained 28 (1.30 g, 0.79 mmol, 66%, $R_f^A$ 0.35): mp 133-134° C.; HRMS (electrospray) Calcd for $C_{110}H_{112}N_5O_8$ [M+H]$^+$: 1630.8510, found: 1630.8505, Calcd for $C_{110}H_{112}N_5O_8Na$ [M+Na]$^+$: 1652.8330, found: 1652.8341.

Compound 32. Azido derivative 31 (1.50 g, 0.84 mmol), triphenylphosphine (1.10 g, 4.21 mmol), amino derivative obtained 32 (1.10 g, 0.63 mmol, 75%, $R_f^B$ 0.65): mp 114-115° C.; HRMS (electrospray) Calcd for $C_{116}H_{125}N_7O_8$ [M+H]$^+$: 1729.9558, found: 1729.9548, Calcd for $C_{110}H_{111}N_5O_8Na$ [M+Na]$^+$: 1751.7326, found: 1751.7317.

EXAMPLE 6

Synthesis of Conjugates Through Formation of an Amide Function

Coupling Reaction with a Carboxylic Acid. The carboxylic acid was dissolved in dichloromethane or DMF under Ar, then 1-[3-(dimethylaminopropyl)]-3-ethylcarbodiimide hydrochloride (EDC) and 1-hydroxybenzotriazole (HOBt) were added. The mixture was stirred for 30 minutes and the neamine derivative was added. The mixture was stirred at room temperature for 1 hour. For the histine conjugates, at the end of reaction, piperidine was added and the resulting solution was stirred at room temperature for 30 minutes until complete removal of the Fmoc protective group. Dichloromethane was added and the resulting solution was washed twice with water, dried over Na$_2$SO$_4$ and evaporated. The residue was chromatographed on alumina gel in CH$_2$Cl$_2$-MeOH (100:0 to 95:5) for obtaining the protected conjugate.

Deprotection. To a solution of the protected conjugate in anisole, was added trifluoroacetic acid. The solution was stirred at room temperature for 12 hours and then methanol was added. The resulting solution was evaporated, then the crude residue was taken up in water, washed with CH$_2$Cl$_2$, and the water phase was concentrated. The residue was chromatographed on Cl$_{18}$ reversed-phase in water. After concentration, the residue was chromatographed on an ion-exchange resin (Amberlite CG-50, NH$_4^+$form) in aqueous ammonia (6%) to afford the deprotected conjugate as the free base. This base was dissolved in 1 M aqueous HCl and the solution was lyophilised to afford the hydrochloride salt of the conjugate.

EXAMPLE 7

Deprotected Amino Derivatives 25, 29, 33

Amino Derivative 25. Neamine derivative 24 (600 mg, 0.34 mmol), deprotected hydrochloride 25 (166 mg, 0.27 mmol, 79%): mp 230° C. dec; $^1$H NMR (400 MHz, D$_2$O) ι 5.76 (d, J$_{1'-2'}$=3.8 Hz, 1H, H1'), 3.82-4.10 (m, 4H, H3', H4, CH$_2$O, H5'), 3.60-3.78 (m, 3H, H5, H6, CH$_2$O), 3.40-3.60 (m, 4H, H3, H2', H6', H4'), 3.20-3.38 (m, 2H, , H6', H1), 2.90 (m, 2H, CH$_2$N), 2.42 (ddd, J$_{2eq-1}$=J$_{2eq-3}$=4.1 Hz, J$_{2eq-2ax}$=12.6 Hz, chain); $^{13}$C NMR (100 MHz, D$_2$O) δ 92.9 (C1'), 82.6 (C-5), 73.1 (C-4), 72.6 (C-6), 72.2 (CH$_2$O), 70.2 (C-4'), 69.9 (C-5'), 68.3 (C-3'), 53.3 (C-2'), 49.8 (C-1), 48.9 (C-3), 40.2 (C-6'), 39.4 (CH$_2$NH), 29.1, 27.8 (C-2), 26.6, 25.5, 24.6 (4CH$_2$ chain); LRMS (electrospray) m/z=444.3 [M+Na]$^+$, 262.2 [5-modified deoxystreptamine +H]$^+$; HRMS (electrospray), Calcd for $C_{18}H_{40}N_5O_6$ [M+H]$^+$: 422.2979, found: 422.2979.

Amino Derivative 30. Neamine derivative 28 (600 mg, 0.37 mmol), deprotected hydrochloride 30 (188 mg, 0.31 mmol, 86%): mp 220° C. dec; $^1$H NMR. (400 MHz, D$_2$O) δ 5.91 (d, J$_{1'-2'}$=3.8 Hz, 1H, H1'), 3.92-4.08 (m, 3H, H3', H5', H4), 3.78-3.88 (m, 1H, CH$_2$O), 3.60-3.70 (m, 2H, H5, CH$_2$O), 3.38-3.58 (m, 4H, H6, H3, H6', H2'), 3.20-3.38 (m, 3H, H1, H4', H6'), 2.92 (m, 2H, CH$_2$N), 2.49 (ddd, J$_{2eq-1}$=J$_{2eq-3}$=4.1 Hz, J$_{2eg-2ax}$=12.6 Hz, 1H, H2$^{2eq}$), 1.90 (ddd, J$_{2ax-1}$=J$_{2ax-3}$=J$_{2eq-2ax}$=12.6 Hz, 1H, H2$_{ax}$), 1.50-1.68 (m, 4H, 2CH$_2$ chain), 1.28-1.38 (m, 4H, 2CH$_2$ chain); $^{13}$C NMR (100 MHz, D$_2$O) δ 95.7 (C-1'), 79.0 (C-4'), 77.2 (C-4), 75.2 (C-5), 73.8 (CH$_2$O), 72.5 (C-6), 68.7 (C-5'), 68.3 (C-3'), 53.6 (C-2'), 49.8 (C-1), 48.6 (C-3), 40.3 (C-6'), 39.1 (CH$_2$NH), 29.4, 28.6 (C-2'), 27.0, 25.8, 25.0 (4CH$_2$ chain); HRMS (electrospray) Calcd for $C_{18}H_{39}N_5O_6Na$ [M+Na]$^+$: 444.2798, found: 444.2796.

Amino Derivative 33. Neamine derivative 32 (600 mg, 0.35 mmol), deprotected hydrochloride 33 (166 mg, 0.22 mol, 64%): mp 220° C. dec; $^1$H NMR. (400 MHz, D$_2$O) δ 5.60 (d, J$_{1'-2'}$=3.8 Hz, 1H, H1'), 3.99-4.03 (m, 1H), 3.87-4.92 (m, 2H), 3.75-3.95 (m, 1H), 3.59-3.62 (m, 2H), 3.47-3.54 (m, 3H), 3.34-3.40 (m, 2H), 3.18-3.25(m, 4H), 2.76-2.80 (m, 4H, 2CH$_2$N), 2.30 (ddd, J$_{2eq-1}$=J$_{2eq-3}$=4.1 Hz, J$_{2eg-2ax}$=12.6 Hz, 1H, H2$^{eq}$), 1.72 (ddd, J$_{2ax-1}$=J$_{2ax-3}$=J$_{2eq-2ax}$=12.6 Hz, 1H, H2$_{ax}$), 1.38-1.48 (m, 8H, 4CH$_2$ chain), 1.17-1.19 (m, 8H, 4CH$_2$ chain); $^{13}$C NMR (50 MHz, D$_2$O) δ 96.9 (C1'), [83.3, 79.4, 79.0, 74.3, 72.8, 72.1, 68.2] (6CH nea, CH$_2$O), [54.7, 50.1, 49.1] (3CH nea,), [40.3, 39.0] (C6', CH$_2$NH), [32.0, 28.7, 28.6, 26.1, 25.0, 24.9, 24.2] (8CH$_2$ chain, C2); LRMS (electrospray) m/z=543.4 [M+Na]$^+$, 262.2 [5-modified deoxystreptamine+H]$^+$; HRMS (electrospray) Calcd for $C_{24}H_{52}N_6O_6Na$ [M+Na]$^+$: 543.3846, found: 543.3846.

EXAMPLE 8

Conjugates at the 5-Position

Histidine conjugate 44. Histidine derivative 34 (540 mg, 0.46 mmol; purchased from Bachem, King of Prussia, Pa.), CH$_2$Cl$_2$ (6 mL), EDC (178 mg, 0.93 mmol), HOBt (126 mg, 0.93 mmol), neamine derivative 24 (540 mg, 0.31 mmol), deprotected conjugate hydrochloride 44 (133 mg, 0.18 mmol, 58%): mp 220° C. dec; $^1$H NMR (500 MHz, D$_2$O) δ 8.60 (s, 1H, H Im), 7.33 (s, 1H, H Im), 5.76 (d, J$_{1'-2'}$=3.8 Hz, 1H, H1'), 4.11 (t, J=7.0 Hz, 1H, CH His), 3.95-4.01 (m, 2H, H3', H4), 3.84-3.95 (m, 2H, CH$_2$O, H5'), 3.60-3.75 (m, 3H, H5, H6, CH$_2$O), 3.40-3.55 (m, 4H, H3, H2', H6', H4'), 3.22-3.35 (m, 4H, CH$_2$ His, H6', H1), 3.01-3.15 (m, 2H, CH$_2$N), 2.40 (ddd, J$_{2eq-1}$=J$_{2eq-3}$=4.1 Hz, J$_{2eq-2ax}$=12.6 Hz, 1H, H2$^{eq}$), 1.82 (ddd, J$_{2ax-1}$=J$_{2ax-3}$=J$_{2eq-2ax}$=12.6 Hz, 1H, H2$_{ax}$), 1.46-1.58 (m, 2H, CH$_2$ chain), 1.30-1.40 (m, 2H, CH$_2$ chain), 1.10-1.30 (m, 4H, 2CH$_2$ chain); $^{13}$C NMR (50 MHz, D$_2$O) δ 167.8 (CO), [134.7, 126.4, 118.7] (3C Im), 93.3 (C1'), [82.9, 73.6, 73.0, 72.6, 70.5, 70.4, 68.6] (6CH nea, CH$_2$O), [53.6, 52.7, 50.2, 49.3] (3CH nea, CH His), [40.5, 39.9] (C6', CH$_2$NH), [29.6, 28.3, 28.2, 26.5, 26.2, 25.0] (4CH$_2$ chain, C2, CH$_2$ His); LRMS (electrospray) m/z=581.3 [M+Na]$^+$, 421.2 [5-modified deoxystreptamine+Na]$^+$; HRMS (electrospray) Calcd for C$_{24}$H$_{46}$N$_8$O$_7$Na [M+Na]$^+$: 581.3387, found: 581.3380.

Phenanthroline Conjugate 45. 4-Carboxylic phenanthroline acid 35 (77 mg, 0.34 mmol; prepared in two steps from the corresponding 4-methyl derivative (Kohjiro, et al. (2001) *J. Photochem. Photobiol., A: Chemistry* 145:117-122)), DMF (6 mL), EDC (131 mg, 0.68 mmol), HOBt (92 mg, 0.68 mmol), neamine derivative 24 (400 mg, 0.22 mmol), deprotected conjugate hydrochloride 45 (78 mg, 0.10 mmol, 46%): mp 210° C. dec; $^1$H NMR (600 MHz, D$_2$O) δ 9.22-9.30 (m, 2H, Ar), 9.12-9.16 (m, 1H, Ar), 8.24-8.34 (m, 3H, Ar), 8.02 (d, 1H, Ar), 5.88 (d, J$_{1'-2'}$=3.8 Hz, 1H, H1'), 4.02-4.08 (m, 3H, H4, H3',CH$_2$O), 3.94 (m, 1H, H5'), 3.82 (m, 1H, CH$_2$O), 3.70-3.77 (m, 3H, H2, H5, H6), 3.48-3.62 (m, 6H, H3, H2', H6', H4', CH$_2$N), 3.32-3.42 (m, 2H, H1, H6'), 2.50 (ddd, 1H, H2$^{eq}$), 1.90 (ddd, 1H, H2$_{ax}$), 1.66-1.76 (m, 4H, 2CH$_2$ chain), 1.40-1.52 (m, 4H, 2CH$_2$ chain); $^{13}$C NMR (75 MHz, D$_2$O) δ 168.8 (CO), [151.0, 145.9, 144.5, 143.2, 139.8, 137.65, 130.1, 127.2, 126.3, 126.1, 125.4, 123.7] (C phen), 93.4 (C1'), [83.0, 73.6, 73.1, 72.8, 70.5, 70.4, 68.7] (6CH nea, CH$_2$O), [53.1, 50.2, 49.3] (3CH nea), [40.5, 39.9] (C6', CH$_2$NH), [29.7, 28.6, 28.2, 26.5, 25.2] (4CH$_2$ chain, C2); LRMS (electrospray) m/z=650.3 [M+Na]$^+$, 468.5 [5-modified deoxystreptamine+H]$^+$; HRMS (electrospray) Calcd for C$_{31}$H$_{45}$N$_7$O$_7$Na [M+Na]$^+$: 650.3278, found: 650.3280.

Flavin conjugate 46. Flavin carboxylic acid 36 (120 mg, 0.34 mmol; prepared according to well-known methods (Frier, et al. (1997) *J. Org. Chem.* 62:3520-3528)), DMF (6 mL), EDC (126 mg, 0.66 mmol), HOBt (89 mg, 0.66 mmol), neamine derivative 24 (400 mg, 0.22 mmol), deprotected conjugate hydrochloride 46 (120 mg, 0.13 mmol, 60%): mp 200° C. dec; $^1$H NMR (400 MHz, D$_2$O) δ 7.47 (s, 1 H, H Fl), 7.43 (s, 1 H, H Fl), 5.69 (d, J$_{1'-2'}$=3.8 Hz, 1H, H1'), 4.41 (m, 1H, CH$_2$-Fl), 3.88-3.94 (m, 2H, H3', H4), 3.78-3.87 (m, 2H, CH$_2$O, H5'), 3.52-3.63 (m, 3H, CH$_2$O, H5, H6), 3.33-3.50 (m, 4H, H3, H2', H6', H4'), 3.17-3.28 (m, 2H, H6', H1), 2.92 (t, J=6.9 Hz, 2H, CH$_2$N), 2.32-2.36 (m, 4H, H2$_{eq}$, CH$_3$ Fl), 2.23 (s, 3H, CH$_3$ Fl), 2.08 (t, 2H, J=7.2 Hz, CH$_2$CO), 1.76 (ddd, J$_{2ax-1}$=J$_{2ax-3}$=J$_{2eq-2ax}$=12.6 Hz, 1H, H2$_{ax}$), 1.63-1.70 (m, 2H, CH$_2$ chain), 1.45-1.53 (m, 2H, CH$_2$ chain), 1.35-1.45 (m, 2H, CH$_2$ chain), 1.18-1.33 (m, 4H, 2CH$_2$ chain), 1.05-1.15 (m, 4H, 2CH$_2$ chain); $^{13}$C NMR (50 MHz, D$_2$O) δ 176.0 (CO), [160.7, 157.3, 150.3, 148.7, 138.7, 134.0, 133.5, 130.5, 130.1, 115.8] (1C Fl), 92.5 (C1'), [82.1, 72.9, 72.2, 71.8, 69.7, 67.8] (6CH nea, CH$_2$O), [52.8, 49.4, 48.5] (3CH nea), 45.2 (CH$_2$N Fl), [39.6, 38.6] (CH$_2$N, C6'), 35.1 (CH$_2$-CO), [28.6, 27.7, 27.4, 25.7, 25.4, 24.8, 24.5, 24.2] (7CH$_2$, C2), 20.3, (CH$_3$), 18.2 (CH$_3$); LRMS (electrospray) m/z=782.4 [M+Na]$^+$, 600.3 [5-modified deoxystreptamine+H]$^+$; HRMS (electrospray) Calcd for C$_{36}$H$_{57}$N$_9$O$_9$Na [M+Na]$^+$: 782.4176, found: 782.4178.

Example 9

Conjugates at the 4'-Position

Histidine Conjugate 47. Histidine derivative 34 (743 mg, 1.20 mmol), CH$_2$Cl$_2$ (6 mL), EDC (460 mg, 2.4 mmol), HOBt (324 mg, 2.4 mmol), neamine derivative 28 (650 mg, 0.39 mol), deprotected conjugate hydrochloride 47 (170 mg, 0.23 mol, 59%): mp 225° C. dec; $^1$H NMR (500 MHz, D$_2$O) δ 8.60 (s, 1H, H Im), 7.33 (s, 1H, H Im) 5.86 (d, J$_{1'-2'}$=3.8 Hz, 1H, H1'), 4.11 (t, J=6.7 Hz, 1H, H His), 3.97-4.02 (m, 1H, H3'), 3.85-3.97 (m, 2H, H5', H4), 3.78-3.83 (m, 1H, CH$_2$O), 3.58-3.67 (m, 2H, H5, CH$_2$O), 3.35-3.55 (m, 4H, H6, H3, H6', H2'), 3.18-3.32 (m, 4H, H1, H4', H6'), 3.03-3.18 (m, 2H, CH$_2$N), 2.43 (ddd, J$_{2eq-1}$=J$_{2eq-3}$=4.1 Hz, J$_{2eq-2ax}$=12.6 Hz, 1H, H2$^{eq}$), 1.83 (ddd, J$_{2ax-1}$=J$_{2ax-3}$=J$_{2eq-2ax}$=12.6 Hz, 1H, H2$_{ax}$), 1.48-1.58 (m, 2H, CH$_2$ chain), 1.28-1.38 (m, 2H, CH$_2$ chain), 1.18-1.28 (m, 2H, CH$_2$ chain), 1.08-1.18 (m, 2H, CH$_2$ chain); $^{13}$C NMR (100 MHz, D$_2$O) δ 167.5 (CO), [134.2, 126.2, 118.2] (3C Im), 95.5 (C1'), [79.0, 77.4, 75.1, 74.0, 72.4,. 68.6, 68.3] (6CH nea, CH$_2$O), [53.5, 52.3, 49.6, 48.4] (3CH nea, CH His), [40.1, 39.5] (C6', CH$_2$NH), [29.1, 28.2, 27.9, 26.1, 25.7, 24.6] (4CH$_2$ chain, C2, CH$_2$ His); HRMS (electrospray) Calcd for C$_{24}$H$_{46}$N$_8$O$_7$Na [M+Na]$^+$: 581.3387, found: 581.3388.

Phenanthroline Conjugate 48. 4-Carboxylic phenanthroline acid 35 (82 mg, 0.36 mmol), DMF (6 mL), EDC (140 mg, 0.73 mmol), HOBt (99 mg, 0.73 mmol), neamine derivative 28 (400 mg, 0.22 mmol), deprotected conjugate hydrochloride 48 (110 mg, 0.14 mmol, 59%): mp 220° C. dec; $^1$H NMR (600 MHz, D$_2$O) δ 9.22-9.30 (m, 2H, Ar), 9.12-9.16 (m, 1H, Ar), 8.24-8.34 (m, 3H, Ar), 8.02 (d, 1H, Ar), 5.94 (d, J$_{1'-2'}$=3.8 Hz, 1H, H1'), 4.09 (m, 1H, H3'), 4.02 (m, 1H, H5'), 3.92-4.00 (m, 2H, H4, CH$_2$O), 3.76 (m, 1H, CH$_2$O), 3.70 (m, 1H, H5), 3.53-3.62 (m, 4H, H3, H6, CH$_2$N), 3.48-3.52 (m, 2H, H6', H2'), 3.40 (m, 1H, H4'), 3.30-3.38 (m, 2H, H6', H1), 2.52 (ddd, 1H, H2$_{eq}$), 1.90 (ddd, 1H, H2$_{ax}$), 1.62-1.78 (m, 4H, 2CH$_2$ chain), 1.40-1.54 (m, 4H, 2CH$_2$ chain); $^{13}$C NMR (75 MHz, D$_2$O) δ 168.8 (CO), [151.0, 146.0, 144.4, 143.3, 139.7, 137.5, 130.1, 127.2, 126.35, 126.1, 125.4, 123.7] (C Phen), 96.1 (C1'), [79.4, 77.9, 75.5, 74.5, 72.9, 69.1, 68.7] (6CH nea, CH$_2$O), 53.9, 50.0, 48.8 (3CH nea), [40.51, 40.47] (C6, CH$_2$NH), [29.6, 28.6, 28.55, 26.4, 25.2] (4CH$_2$ chain, C2); HRMS (electrospray) Calcd for C$_{31}$H$_{46}$N$_7$O$_7$ [M+H]$^+$: 628.3458, found: 628.3452, Calcd for C$_{31}$H$_{45}$N$_7$O$_7$Na [M+Na]$^+$: 650.3278, found: 650.3267.

EXAMPLE 10

Conjugates at the 4'- and 5-Positions

Histidine conjugate 49. Histidine derivative 34 (682 mg, 1.10 mmol), CH$_2$Cl$_2$ (15 mL), EDC (432 mg, 2.20 mmol), HOBt (305 mg, 2.20 mmol), neamine derivative 32 (650 mg, 0.37 mmol), deprotected conjugate hydrochloride 49 (106 mg, 0.10 mmol, 27%): mp 210° C. dec; $^1$H NMR (400 MHz, D$_2$O) δ 8.36 (s, 1H, H Im), 8.34 (s, 1H, H Im), 7.18 (s, 2H, H Im), 5.62 (d, J$_{1'-2'}$=3.8 Hz, 1H, H1'), 3.99-4.01 (m, 2H, H His), 3.77-4.95 (m, 3H), 3.45-3.68 (m, 6H), 3.33-3.43 (m, 2H), 3.13-3.32 (m, 6H), 2.92-3.11 (m, 6H), 2.30 (ddd, 1H, H2$^{eq}$), 1.72 (ddd, 1H, H2$_{ax}$), 1.38-1.53 (m, 4H, 2CH$_2$), 1.20-1.30 (m, 4H, 2CH$_2$), 1.10-1.20 (m, 4H, 2CH$_2$), 1.00-1.10 (m, 4H, 2CH$_2$); $^{13}$C NMR (100 MHz, D$_2$O) δ 168.3 (CO), [135.0, 127.5, 118.4] (C Im), 92.79 (C1'), [83.1, 78.1, 74.6, 73.7, 73.3, 73.1, 70.6, 68.2] (6CH nea, 2CH$_2$O), [53.3, 52.9, 50.2, 49.2] (3CH nea, CH His), [40.2, 40.0, 39.9] (C6', 2CH$_2$NH), [29.7, 29.5, 28.4, 27.1, 27.1, 26.3, 26.2, 25.1, 25.1, 23.6] (8CH$_2$ chain, C2, 2CH$_2$ His); LRMS (electrospray) m/z=817.5 [M+Na]$^+$, 399.2 [5-modified deoxystreptamine+H]$^+$; HRMS (electrospray) Calcd for C$_{36}$H$_{66}$N$_{12}$O$_8$Na [M+Na]$^+$: 817.5024, found: 817.5016.

Phenanthroline Conjugate 50. 4-Carboxylic phenanthroline acid 35 (136 mg, 0.61 mmol), DMF (6 mL), EDC (236 mg, 1.20 mmol), HOBt (164 mg, 1.20 mmol), neamine derivative 32 (350 mg, 0.20 mmol), deprotected conjugate hydrochloride 50 (110 mg, 0.04 mmol, 22%): mp 220° C. dec; $^1$H NMR (600 MHz, D$_2$O) δ 9.10-9.18 (m, 4H, Ar), 8.96-9.99 (m, 2H, Ar), 8.06-8.21 (m, 6H, Ar), 7.92-7.98 (m, 4H, Ar), 5.81 (d, J$_{1'-2'}$=3.8 Hz, 1H, H1'), 4.18-4.22 (m, 1H), 4.04-4.14 (m, 3H), 3.80-3.86 (m, 2H), 3.68-3.78 (m, 3H), 3.50-3.62 (m, 6H), 3.34-3.50 (m, 4H), 2.52 (ddd, 1H, H2$^{eq}$), 1.90 (ddd, 1H, H2$_{ax}$), 1.62-1.78 (m, 8H, CH$_2$), 1.40-1.54 (m, 8H, CH$_2$); $^{13}$C NMR (75 MHz, D$_2$O) δ 168.6 (CO), [151.0, 150.9, 145.6, 144.6, 143.2, 143.1, 139.7, 137.5, 129.8, 127.2, 127.1, 126.4, 126.2, 126.1, 126.0, 125.9, 125.4, 123.74, 123.65, 123.62] (Ar), 92.8 (C1'), [82.9, 78.0, 74.7, 73.6, 73.4, 73.2, 70.9, 68.3] (6CH nea, 2CH$_2$O), [55.7, 55.3, 53.3, 50.1, 49.2] (CH nea), [40.4, 40.2, 40.1] (C6', 2CH$_2$NH), [29.6, 29.4, 28.6, 28.5, 28.2, 26.5, 26.3, 25.3, 25.1] (8CH$_2$ chain, C2); LRMS (electrospray) m/z=955.5 [M+Na]$^+$, 468.3 [5-modified deoxystreptamine+H]$^+$; HRMS (electrospray) Calcd for C$_{50}$H$_{64}$N$_{10}$O$_8$Na [M+Na]$^+$: 955.4806, found: 955.4805.

EXAMPLE 11

Adenine Conjugates 55, 57, and 59

Coupling Reaction. To a solution of the neamine derivative 24, 28 or 32 in EtOH/THF/Et$_3$N (10/0.5/0.6 mL), 6-chloropurine was added and the mixture was refluxed for 4 hours. After cooling, dichloromethane was added (50 mL). The resulting solution was washed twice with water (50 mL), dried over Na$_2$SO$_4$ and evaporated. The residue obtained was treated for deprotection according to the work-up described for the conjugates possessing an amide function.

Conjugate at the 5-Position 55. Neamine derivative 24 (490 mg, 0.28 mmol) in EtOH/THF/Et$_3$N (10/0.5/0.6 mL), 6-chloropurine (441 mg, 2.85 mmol), deprotected conjugate hydrochloride 55 (151 mg, 0.21 mmol, 75%): mp 210° C. dec; $^1$H NMR (400 MHz, D$_2$O) δ 8.36 (s, 1H, H Pu), 8.25 (s, 1H, H Pu), 5.77 (d, J$_{1'-2'}$=3.8 Hz, 1H, H1'), 3.83-4.03 (m, 4H, H3', H4, H5', CH$_2$O), 3.61-3.75 (m, 3H, H5, H6, CH$_2$O), 3.49-3.58 (m, 2H, CH$_2$N), 3.39-3.48 (m, 4H, H3, H2', H6', H4'), 3.22-3.35 (m, 2H, H6', H1), 2.40 (ddd, J$_{2eg-1}$=J$_{2eg-3}$=4.1Hz, J$_{2eq-2ax}$=12.6 Hz, 1H, H2$^{eq}$), 1.85 (ddd, J$_{2ax-1}$=J$_{2ax-3}$=J$_{2eq-2ax}$=12.6 Hz, 1H, H2$_{ax}$), 1.63-1.71 (m, 2H, CH$_2$ chain), 1.51-1.60 (m, 2H, CH$_2$ chain), 1.28-1.42 (m, 4H, 2CH$_2$ chain); $^{13}$C NMR (50 MHz, D$_2$O) δ [144.8, 142.6] (C Pu), 92.6 (C1'), [82.6, 72.9, 72.2, 71.8, 69.7, 67.6] (CH nea, CH$_2$O), [52.8, 49.4, 48.5] (3 CH nea), 39.6 (C6', CH$_2$NH), [28.8, 27.4, 25.4, 24.3] (CH$_2$ chain, C2); LRMS (electrospray) m/z=540.3 [M+H]$^+$, 380.2 [5-modified deoxystreptamine+H]$^+$; HRMS (electrospray) Calcd for C$_{23}$H$_{42}$N$_9$O$_6$ [M+H]$^+$: 540.3258, found: 540.3252, Calcd for C$_{23}$H$_{41}$N$_9$O$_6$Na [M+Na]$^+$: 562.3077, found: 562.3091.

Conjugate at the 4'-Position 57. Neamine derivative 28 (500 mg, 0.31 mmol) in EtOH/THF/Et$_3$N (10/0.5/0.6 mL), 6-chloropurine (473 mg, 3.05 mmol), deprotected conjugate hydrochloride 57 (160 mg, 0.22 mmol, 73%): mp 220° C. dec; $_1$H NMR (500 MHz, D$_2$O) δ 8.34 (s, 1H, H Pu), 8.24 (s, 1H, H Pu), 5.86 (d, J$_{1'-2'}$=3.8 Hz, 1H, H1'), 3.97-4.01 (m, 1H, H3'), 3.88-3.95 (m, 2H, H5', H4), 3.78-3.83 (m, 1H, CH$_2$O), 3.58-3.67 (m, 2H, H5, CH$_2$O), 3.43-3.58 (m, 4H, H6, H3, CH$_2$N), 3.37-3.43 (m, 2H, H2', H3) 3.18-3.31 (m, 3H, H4', H1, H6') 2.43 (ddd, J$_{2eq-1}$=J$_{2eq-3}$=4.1Hz, J$_{2eq-2ax}$=12.6 Hz, 1H, H2$^{eq}$), 1.83 (ddd, J$_{2ax-1}$=J$_{2ax-3}$=J$_{2eq-2ax}$=12.6 Hz, 1H, H2$_{ax}$), 1.63-1.71 (m, 2H, CH$_2$ chain), 1.51-1.60 (m, 2H, CH$_2$ chain), 1.28-1.42 (m, 4H, 2CH$_2$ chain); $^{13}$C NMR (100 MHz, D$_2$O) δ 143.4 (C Pu), 96.1 (C1'), [79.4, 77.9, 75.5, 74.4, 72.9, 69.0, 68.7] (6CH nea, CH$_2$O), [53.9, 50.0, 48.8] (3CH nea), [40.5, 40.3] (C6', CH$_2$NH), [29.6, 28.6, 28.1, 26.1, 25.2] (4CH$_2$ chain, C2); HRMS (electrospray) Calcd for C$_{23}$H$_{42}$N$_9$O$_6$ [M+H]$^+$: 540.3258, found: 540.3282, Calcd for C$_{23}$H$_{41}$N$_9$O$_6$Na [M+Na]$^+$: 562.3077, found: 562.3078, Calcd for C$_{23}$H$_{41}$N$_9$O$_6$K [M+K]$^+$: 578.2816, found: 578.2823.

Conjugate at the 4'- and 5-Positions 59. Neamine derivative 32 (500 mg, 0.29 mmol) in EtOH-THF-Et$_3$N (10/0.5/0.6 mL), 6-chloropurine (447 mg, 2.89 mmol), deprotected conjugate hydrochloride 59 (180 mg, 0.18 mmol, 63%): mp 230° C. dec; $^1$H NMR (400 MHz, D$_2$O) δ 8.30 (bs, 2H, H Pu), 8.20 (bs, 2H, H Pu), 5.68 (d, J$_{1'-2'}$=3.8 Hz, 1H, H1'), 4.05-4.10 (m, 1H), 3.88-4.01 (m, 3H), 3.65-3.75 (m, 2H), 3.43-3.62 (m, 9H), 3.22-3.38 (m, 4H), 2.40 (ddd, 1H, H2$^{eq}$), 1.82 (ddd, 1H, H2$_{ax}$), 1.62-1.73 (m, 4H, 2CH$_2$ chain), 1.50-1.60 (m, 4H, 2CH$_2$ chain), 1.25-1.42 (m, 8H, 4CH$_2$); $^{13}$C NMR (100 MHz, D$_2$O) δ 142.9 (C Pu), 92.8 (C1'), [83.0, 78.0, 74.6, 73.6, 73.3, 73.1, 70.8, 68.2] (CH nea, CH$_2$O), [53.2, 50.1, 49.2] (3CH nea), 40.1 (C6', CH$_2$NH), [29.7, 29.4, 28.2, 28.18, 26.2, 26.1, 25.24, 25.20] (8CH$_2$ chain, C2); LRMS (electrospray) m/z=779.4 [M+Na]$^+$, 380.2 [5-modified deoxystreptamine+H]$^+$; HRMS (electrospray) Calcd for C$_{34}$H$_{57}$N$_{14}$O$_6$ [M+H]$^+$: 757.4585, found: 757.4595, Calcd for C$_{34}$H$_{56}$N$_{14}$O$_6$Na [M+Na]$^+$: 779.4405, found: 779.4404, Calcd for C$_{34}$H$_{56}$N$_{14}$O$_6$K [M+K]$^+$: 795.4144, found: 795.4133.

EXAMPLE 12

Synthesis of Dimer 53 (Scheme 6)

Succinic derivative 51. To a solution of the neamine derivative 24 (1.0 g, 0.57 mmol) in dichloromethane (10 mL), triethylamine (160 μL, 1.14 mmol) and succinic anhydride (69 mg, 0.69 mmol) were successively added. The solution was stirred for 1 hour at room temperature and dichloromethane was added (90 mL). The resulting solution was washed twice with water (50 mL), dried over Na$_2$SO$_4$ and evaporated. The residue was chromatographed on silica gel with CH$_2$Cl$_2$-methanol-triethylamine (95:4:1) resulting in compound 51 (1.0 g, 0.51 mmol, 90%): mp 124-126° C.; LRMS (FAB$^+$, NBA) m/z=1874 [MCOONa+H]$^+$, 1896 [MCOONa$_2$]$^+$; HRMS (electrospray) Calcd for C$_{122}$H$_{124}$N$_5$O$_{12}$ [M+H]$^+$: 1850.9246, found: 1850.9209.

Dimer 53. Succinic acid-neamine derivative 51 (200 mg, 0.10 mmol), dichloromethane (4 mL), EDC (29 mg, 0.15 mmol), HOBt (21 mg, 0.15 mmol), neamine derivative 24 (214 mg, 0.12 mmol), deprotected conjugate hydrochloride 37 (100 mg, 0.08 mmol, 80%): mp 210° C. dec; $^1$H NMR (500 MHz, D$_2$O) δ 5.76 (d, J$_{1'-2'}$=3.7 Hz, 1H, H1'), 3.84-4.01 (m, 4H, H3', H4, H5', CH$_2$O), 3.60-3.75 (m, 3H, H5, H6, CH$_2$O), 3.40-3.55 (m, 4H, H3, H2', H6', H4'), 3.22-3.35 (m, 2H, H6', H1), 3.06 (t, J=7 Hz, 2H, CH$_2$N), 2.40 (m, 3H, H2$^{eg}$, CH$_2$), 1.82 (ddd, J$_{2ax-1}$=J$_{2ax-3}$=J$_{2eq-2ax}$=12.6 Hz, 1H, H2$_{ax}$) 1.46-1.58 (m, 2H, CH$_2$ chain), 1.30-1.40 (m, 2H, CH$_2$ chain), 1.10-1.30 (m, 4H, 2CH$_2$ chain); $^{13}$C NMR (75 MHz, D$_2$O) δ 174.0 (CO), 92.05 (C1'), [82.1, 72.9, 72.1, 71.6, 69.6, 67.6] (6CH nea, CH$_2$O), [52.8, 49.3, 48.5] (3CH nea), [39.6, 38.6] (C6', CH$_2$NH), [31.0, 28.6, 27.8, 27.4, 25.4, 24.3] (5CH$_2$ chain, C2); HRMS (electrospray) Calcd for C$_{40}$H$_{80}$N$_{10}$O$_{14}$Na [M+Na]$^+$: 947.5753, found: 947.5734.

EXAMPLE 13

Synthesis of Compound 60

In the synthesis of an anti-TAR PNA-Neamine conjugate 60 the protected neamine monomer 51, possessing a carboxylate group necessary for coupling the neamine core to the terminal amino function of the protected PNA, was synthesized in six steps: (1) protection of the four amino functions by reaction of neamine 18 with trityl chloride in triethylamine (80% yield) (See Scheme 1, compound 19), (2) protection of the 3', 5' and 6-hydroxyl functions with 4-methoxybenzyl groups (Scheme 1, compound 20, the 5-hydroxyl function is the most hindered hydroxyl function and thus the less reactive), (3) introduction at the 5-position of a hexyl linking chain possessing a terminal bromine atom by reaction of the 5-hydroxyl function with 1,6-dibromohexane in the presence of NaH (Scheme 2, compound 22), (4 and 5) substitution of the terminal bromine atom for an azido group (compound 23) and, then, reduction, to obtain, at the end of the hexyl linking chain, an amino function (compound 24), and (6) reaction of this amino function with succinic anhydride for obtaining the neamine monomer 51.

The neamine monomer 51 was coupled to a protected 16-mer anti-TAR PNA (5'-TCC CAG GCT CAG ATC T-3', SEQ ID NO:1) attached to its solid support of synthesis using EDC/HOBt as coupling agents. Deprotection of the neamine core and the PNA bases and concomitant cleavage from the solid support were performed in one step in TFA/anisole (1:1). The resulting conjugate (Compound 60) was purified by HPLC on C$_{18}$ reversed-phase (50% coupling yield) and its structure was confirmed by mass spectrometry (MALDI) according to standard methods.

PNA-Neamine Conjugate 60. The protected neamine derivative 51 (39 mg, 20 μmol) was dissolved in DMF (100 μL) under Ar and, then, 1-[3-dimethylaminopropyl)]-3-ethylcarbodiimide hydrochloride (EDC) (5.7 mg, 30 μmol) and 1-hydroxybenzotriazole (HOBt) (4 mg, 30 μmol) were added. The resulting solution was stirred for 15 minutes and was added under Ar to the protected PNA on the solid support (PNA synthesis at 2 μM scale). The mixture was stirred at room temperature for 1 hour and filtered.

The neamine-PNA conjugate was cleaved from the solid support with concomitant deprotection by treatment with TFA/anisole for 1 hour. The mixture was filtered and, subsequently, diethyl ether was added to the solution to precipitate the neamine-PNA conjugate (Compound 60).

HPLC purification was carried out on a C$_{18}$ reversed-phase column (Macherey-Nagel, 10.0 x 25.0 mm). Elution was performed at 60° C. by building up the following gradient at a flow rate of 1.5 mL·min$^{-1}$: 0.1% TFA in acetonitrile/0.1% TFA in water 10/90 v/v, 10 minutes, then 0.1% TFA in acetonitrile/0.1% TFA in water/methanol 10/85/5 v/v. Under these conditions the deprotected unreacted PNA 18 and the conjugate 60 were separated and characterized by mass spectrometry. After freeze-drying, 45 nmol of PNA 1 and 45 nmol of conjugate 60 were obtained (50% estimated coupling yield).

MALDI-TOF MS, conjugate 60, m/z: found, 4792.61, calculated for C$_{192}$H$_{256}$N$_{94}$O$_{57}$, 4792.68.

EXAMPLE 14

Biochemistry and Biological Assays

Preparation of HIV-1 TAR RNA. The labeled and unlabeled run-off transcript of HIV-1 TAR RNA was prepared from plasmid pEM-7 linearized with HindIII using standard methods (Moazed and Noller (1987) Nature 327:389-394). The labeled transcript was purified by 10% polyacrylamide-urea gel electrophoresis. The radioactive band was excised from the gel, extracted in 0.5 M ammonium acetate, desalted on a NAP-10 column (Pharmacia, Inc., Piscataway, N.J.), lyophilized, and dissolved in 10 mM Tris-HCl, pH 7.8, 60 mM KCl and 10 mM DTT and stored at −70° C. The specific radioactivity of the resulting purified transcript was determined by A$_{260}$ absorbance and Cerenkov counting.

Gel Retardation Assay. The binding affinity of PNA$_{TAR}$-neamine conjugate for TAR RNA was evaluated by gel mobility shift analysis according to standard methods (Zhou, et al. (2003) supra; Kaushik, et al. (2002) supra; Moazed and Noller (1987) supra). In brief, anti-TAR PNAs at varying molar ratios were incubated with the $^{32}$P-labeled TAR RNA transcript (5000 Cerenkov cpm) for 1 hour at 37° C. in a binding buffer containing 50 mM Tris-HCl, pH 7.8, 60 mM KCl, 5.0 mM MgCl$_2$, 10 mM DTT, 10% glycerol, 0.01% NP-40 and 500 ng of r (I-C), in a final volume of 15 μl. Three microliters of RNA gel loading dye (0.27% bromophenol blue and 30% glycerol) was added to the samples prior to loading. Samples were then subjected to polyacrylamide DNA retardation analysis on a native 6% polyacrylamide gel in Tris-Borate buffer. The gels were routinely pre-run at 120 V for 30 minutes at 4° C. in Tris-Borate buffer, pH 8.2. The RNA-PNA complexes were resolved at a constant voltage of 120 V at 4° C. for 3 hours and detected by phosphorimaging.

Reverse Transcription of TAR RNA. Reverse transcription catalyzed by HIV-1 reverse transcriptase on TAR RNA in the presence or absence of the PNA$_{TAR}$-neamine conjugate was monitored by gel extension analysis. A 17-mer DNA primer (TAT TGA GGC TTA AGC AG; SEQ ID NO:2) was 5'-labeled using α-$^{32}$P-ATP and T$_4$ polynucleotide kinase according to standard methods and annealed in a 2:1 molar ratio of RNA template to primer. The PNA$_{TAR}$-neamine conjugate at indicated concentrations were pre-incubated with 10 nM of the annealed template-primer at 25° C. for indicated times in a reaction buffer containing 50 mM Tris-HCl, pH 7.8, 10 mM DTT, 100 μg/mL bovine serum albumin, 60 mM KCl and 5 mM MgCl$_2$ and used in the extension reaction. Reverse transcription was initiated by the addition of 50 nM of HIV-1 reverse transcriptase and 100 μM each of the 4 dNTPs. The products were resolved on an 8% polyacrylamide-urea gel and visualized on a phosphorimager.

PNA-Neamine Conjugate 60 Activity. Since PNA-RNA or PNA-DNA duplexes exhibit higher melting temperatures than corresponding RNA-DNA or DNA-DNA duplexes, it was determined whether the PNA$_{TAR}$-neamine conjugate was able to block reverse transcription of the HIV-1 TAR. Blocking reverse transcription would have multiple effects on viral replication besides influencing Tat-mediated transactivation. For this purpose, TAR RNA primed with the labeled 17-mer DNA primer was incubated in the absence or presence of conjugate 60 at 37° C. followed by initiation of reverse transcription by HIV-1 reverse transcriptase. The results of. these experiments indicated that prominent pauses in reverse transcription occurred at the site targeted by the PNA-neamine conjugate. These results show that the anti-TAR PNA-neamine conjugate binds to its target site on TAR and blocks reverse transcription, probably by inhibiting the strand displacement activity of HIV-1 reverse transcriptase.

Isolation of HIV-1 Virions. The pseudotyped HIV-1 virions were isolated from the culture supernatant of 293T cells transfected with pHIV-1$_{JR-CSF-Luc}$env (-) and pVSV-G clones. The culture supernatant (500 mL) was filtered through 0.45 µm pore size membrane and centrifuged at 70,000 g for 45 minutes. The pelleted virions were resuspended in fresh culture medium containing 10% fetal calf serum and stored at −80° C. HIV-1 virions were quantified by determining the RNA copy number in the sample using NUCLISENS® HIV-1-QT Amplication Kit (Organon Teknika, Durham, N.C.). The virion number was also extrapolated from the p24 concentration considering that 2000 copies of p24 are present per virion particle. The virion number estimated from the RNA copy number was in agreement with the number determined by p24 quantification (1 pg p24 per 12500 virions).

Infection of CEM Cells with HIV-1 S1. Lymphocyte CEM (12D7) cells were maintained in complete RPMI-1640 medium supplemented with 10% fetal bovine serum (FBS), 100 U/mL of penicillin and 100 µg/mL of streptomycin at 37° C. in 5% $CO_2$ containing humidified air. CEM cells were infected with pseudotyped HIV-1 S1 strain and incubated in the presence of indicated concentration of PNA$_{TAR}$-neamine conjugate 60 or naked PNA. Cells were harvested 48 hours after infection, lysed and assayed for luciferase activity according to standard methods (Zhou, et al. (2003) supra).

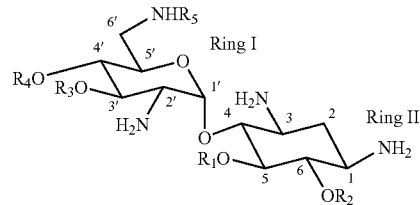

Formula I wherein, at least one of $R_1$, $R_2$, $R_3$, or $R_4$ is a peptide nucleic acid which hybridizes with one or more nucleic acid molecules and the remaining substituents, $R_1$, $R_2$, $R_3$, $R_4$, and $R_5$, are each independently a hydrogen, a neamine, a lipophilic chain, a reactive or catalytic group, or a binding element.

2. A method for producing a composition of claim 1 comprising the steps of:
 a) protecting amino functions of the neamine moiety with an acid-labile protecting group;
 b) protecting hydroxyl functions of the neamine moiety with a protecting group which produces an acid-labile ether;
 c) conjugating $R_1$, $R_2$, $R_3$, $R_4$, or $R_5$ substituents to the neamine moiety, wherein at least one of $R_1$, $R_2$, $R_3$, or $R_4$ is a peptide nucleic acid which hybridizes with one or more nucleic acid molecules; and

What is claimed is:

1. A composition for modulating the activity of a nucleic acid molecule comprising a peptide nucleic acid moiety conjugated to a neamine moiety, wherein said composition is of Formula I d) deprotecting the amino and hydroxyl functions and recovering the peptide nucleic acid-neamine conjugate.

3. A method for modulating the activity of a nucleic acid molecule comprising contacting one or more nucleic acid molecules with a composition of claim 1 which hybridizes with at least one nucleic acid molecule of the one or more nucleic acid molecules so that the function of the at least one nucleic acid molecule is modulated.

4. A method for preventing or treating a disease associated with an aberrant nucleic acid molecule comprising administering to a patient with a disease associated with an aberrant nucleic acid molecule located within a T lymphocyte an effective amount of a composition of claim 1 which hybridizes with the aberrant nucleic acid molecule located within the T lymphocyte so that the function of the aberrant nucleic acid molecule is modulated and the disease associated with said aberrant nucleic acid molecule is prevented or treated.

* * * * *

SEQUENCE LISTING

<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1
tcccaggctc agatct                                              16

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
tattgaggct taagcag                                             17